US009345851B2

(12) United States Patent
Kim et al.

(10) Patent No.: US 9,345,851 B2
(45) Date of Patent: May 24, 2016

(54) DIRECTION SWITCHING VALVE UNIT AND COUGH ASSISTING DEVICE USING THE SAME

(71) Applicant: Seoil Pacific Corp., Seoul (KR)

(72) Inventors: Kye Cheol Kim, Gyeonggi-do (KR); Chil Hwan Kim, Gyeonggi-do (KR)

(73) Assignee: SEOIL PACIFIC CORP, Seoul (KR)

( * ) Notice: Subject to any disclaimer, the term of this patent is extended or adjusted under 35 U.S.C. 154(b) by 605 days.

(21) Appl. No.: 13/840,643

(22) Filed: Mar. 15, 2013

(65) Prior Publication Data

US 2013/0255689 A1 Oct. 3, 2013

(30) Foreign Application Priority Data

Mar. 27, 2012 (KR) ........................ 10-2012-0030979

(51) Int. Cl.
*A61M 16/20* (2006.01)
*A61M 16/00* (2006.01)
(Continued)

(52) U.S. Cl.
CPC ......... *A61M 16/208* (2013.01); *A61M 16/0003* (2014.02); *A61M 16/0006* (2014.02); *A61M 16/0009* (2014.02); *A61M 16/0057* (2013.01); *A61M 16/0063* (2014.02); *A61M 16/0816* (2013.01); *A61M 16/20* (2013.01);
(Continued)

(58) Field of Classification Search
CPC ... F16K 11/085; F16K 11/0856; F16K 31/04; A61M 16/00; A61M 16/0003; A61M 16/0009; A61M 2016/0015; A61M 2016/0018; A61M 16/0057; A61M 16/0063; A61M 16/0066; A61M 16/0069; A61M 16/20; A61M 16/201; A61M 16/202; A61M 16/203; A61M 16/204; A61M 16/205; A61M 16/206; A61M 16/207; A61M 16/208; A61M 2205/3331; A61M 2205/3334; A61M 2205/42; A61M 16/0816; A61M 16/0875
USPC ............................... 137/625.47; 128/205.19; 251/129.11–13
See application file for complete search history.

(56) References Cited

U.S. PATENT DOCUMENTS 2,523,521 A * 9/1950 Ritter ...................... F15B 11/20
137/625.11
2,914,064 A * 11/1959 Sandelowsky ........ A61M 16/20
128/205.19

(Continued)

FOREIGN PATENT DOCUMENTS

KR       10-1038262 B1   6/2011

*Primary Examiner* — Justine Yu
*Assistant Examiner* — Tu Vo
(74) *Attorney, Agent, or Firm* — Rabin & Berdo, P.C.

(57) ABSTRACT

Provided is a direction switching valve unit and a cough assisting device using the same for inhaling to and exhaling from a patient's respiratory organ to induce a cough, the cough assisting device has a case body (100) having an inhaling space (110) formed on and passing through a lower surface thereof; an air pressure generating unit (200) provided in the case body (100), the air pressure generating unit generating an air pressure through a rotation force for suctioning air into an air inlet (210) and discharging suctioned air via an air outlet (220); a direction switching valve unit (300) provided in the inhaling space (110) formed through the case body (100), the direction switching valve unit converting a flow direction of the air for forcedly suctioning air toward a patient's respiratory organ or forcedly discharging air from a patient's respiratory organ by means of air pressure generated in the air pressure generating unit (200), whereby the device can be operated with low electric power.

14 Claims, 21 Drawing Sheets

(51) Int. Cl.
 *A61M 39/22* (2006.01)
 *F16K 11/085* (2006.01)
 *A61M 16/08* (2006.01)
 *A61M 16/06* (2006.01)

(52) U.S. Cl.
 CPC .......... *A61M 16/201* (2014.02); *A61M 16/202* (2014.02); *A61M 16/204* (2014.02); *A61M 16/205* (2014.02); *F16K 11/085* (2013.01); *F16K 11/0856* (2013.01); *A61M 16/0066* (2013.01); *A61M 16/06* (2013.01); *A61M 16/0875* (2013.01); *A61M 2016/0015* (2013.01); *A61M 2016/0018* (2013.01); *A61M 2205/3331* (2013.01); *A61M 2205/3334* (2013.01); *A61M 2205/42* (2013.01)

(56) References Cited

U.S. PATENT DOCUMENTS

| | | | | |
|---|---|---|---|---|
| 3,139,907 A * | 7/1964 | Jones | ............... | E03B 9/02 137/625.29 |
| 4,702,269 A * | 10/1987 | Schuler | ............... | F16K 11/0853 137/246.12 |
| 5,105,851 A * | 4/1992 | Fogelman | ............. | F16K 11/083 137/625.11 |
| 5,172,725 A * | 12/1992 | Kitagawa | ............. | F16K 11/0856 137/625.43 |
| 5,431,189 A * | 7/1995 | Jones | ............... | B60H 1/00585 137/625.42 |
| 5,630,411 A * | 5/1997 | Holscher | ............... | A61M 16/00 128/204.21 |
| 5,746,252 A * | 5/1998 | Henson | ............... | F16K 11/0853 137/375 |
| 5,850,835 A * | 12/1998 | Takaki | ............. | A61M 16/0009 128/204.18 |
| 6,694,976 B1 * | 2/2004 | Takaki | ............. | A61M 16/0096 128/204.18 |
| 8,127,793 B2 * | 3/2012 | Ito | ............... | F16K 11/0853 137/625.47 |
| 2005/0039749 A1 * | 2/2005 | Emerson | ............... | A61M 16/00 128/204.23 |
| 2006/0118066 A1 * | 6/2006 | Martins | ............... | F01P 7/165 123/41.08 |
| 2008/0245077 A1 * | 10/2008 | Xu | ............... | F16K 31/041 62/6 |
| 2012/0285460 A1 * | 11/2012 | Smith | ............... | A61M 16/20 128/205.24 |

\* cited by examiner

DIRECTION SWITCHING VALVE UNIT AND COUGH ASSISTING DEVICE USING THE SAME

BACKGROUND

1. Field of the Invention

The present invention relates to a direction switching valve unit in which a rotating body is miniaturized to reduce a driving electric power to be consumed for rotating/driving the miniaturized rotating body as compared with a conventional device, and air forcedly discharged toward a patient's respiratory organ is guided to allow this air to flow into a case body constituting an external member of a cough assisting device so that as a cough noise contained in the air forcedly discharged toward a patient's respiratory organ collides with the case body, some of the cough noise is damped and then penetrates the case body and the remainder of the cough noise of a patient, which does not penetrate the case body, is reflected and dispersed in the case body or damped and penetrates the case body again to minimize the cough noise and to minimize reabsorption of carbon dioxide and an odor causing substance contained in a cough of patient into air supplied from an outside when the device is repeatedly utilized for inducing a patient to cough, and a means for adjusting amount of forcedly suctioned air under a preset air pressure is provided. The present invention also relates to a cough assisting device using the above direction switching valve unit.

2. Discussion of Related Art

A cough prevents harmful substances such as gas, bacteria and the like and foreign substance from entering a respiratory tract and discharges foreign substances that have entered or secretions in the respiratory tract from the respiratory tract to keep the respiratory tract clean. However, a cough function of a neuromuscular patient suffering from muscle paralysis or a patient with a restrictive lung disease is lowered so that a patient contracts pneumonia caused by a foreign substance or suffers from difficulty in breathing due to secretions blocking the respiratory tract.

As a solution to this, a cough assisting device which supplies air (positive pressure) into a respirator tract of a patient and then rapidly suctions the air (negative pressure) to induce a cough has been proposed.

FIG. 1 is an exploded perspective view of a conventional direction switching valve unit and a cough assisting device using the same invented and registered (Korean Patent No. 10-1038262) by the present inventors; FIG. 2 is an essential perspective view showing an air pressure generating unit, a direction switching valve unit and a connecting box constituting the conventional direction switching valve unit and the cough assisting device using the same; FIG. 3 is an exploded perspective view showing the direction switching valve unit constituting the conventional direction switching valve unit and the cough assisting device using the same; FIG. 4 is a sectional view showing a coupling state of the air pressure generating unit, the direction switching valve unit and the connecting box constituting the conventional direction switching valve unit and the cough assisting device using the same; and FIG. 5 is a sectional view showing a rotating body included in the air pressure generating unit and the direction switching valve unit constituting the conventional direction switching valve unit and the cough assisting device using the same.

In an improved conventional direction switching valve and a cough assisting device using the same, as shown in the drawings, an air pressure generating unit 10, a direction switching valve unit A and a connecting box 50 are provided in a case 60.

First, the air pressure generating unit 10 suctions air generated by a turbo fan rotated by a rotational force transmitted from a motor and flowing through an air inlet 11 and discharges the suctioned air through an air outlet 12. In the air pressure generating unit 10, by adjusting a rotational force of the motor, a pressure of the air supplied or suctioned by the turbo fan is adjusted.

The direction switching valve unit A converts an air flow direction by means of an air pressure generated in the air pressure generating unit 10 to allow air to be forcedly supplied to a patient's respiratory organ or to be forcedly discharged from a patient's respiratory organ. Also, the direction switching valve unit A discharges some of air forcedly caused to flow by the air pressure to an outside or suctions air from an outside to adjust the air pressure.

The direction switching valve unit A performing the above functions consists of a housing 20 including an inlet 21 and an outlet 22 formed on a front surface for allowing air to enter and be discharged therethrough, a first entrance 23 formed on a rear surface for allowing air to enter and be discharged therethrough, a second entrance 24 formed on bottom surface for allowing air to enter and be discharged therethrough, the inlet 21 and the outlet 22 being formed at right and left sides and aligned with each other, the first entrance 23 being formed at a central portion, the inlet 21, the outlet 22 and the first entrance 23 being formed at the same height, and the second entrance 24 being disposed on a central axis of the housing; a rotating body 30 installed axially in the housing 20 and having a horizontal passage 31 extending from the inlet 21 and the outlet 22 to the first entrance 23 of the housing 20 along a rounded outer circumferential surface, a pair of partitions 32a, 32b for dividing a certain region of the horizontal passage 31 and a vertical passage 33 formed at a central portion and extending from the second entrance 24 of the housing 20 to a space between the pair of partitions 32a, 32b; and a two-directional motor 40 provided on an upper portion of the housing 20 and connected to a shaft of the rotating body 30 to adjust a rotation angle of the rotating body 30 in the forward direction or in the reverse direction.

Here, the rotating body 30 has a structure in which a space between a pair of partitions 32a and 32b constituting the rotating body 30 is spread from a shaft at a certain angle to simultaneously cover the inlet 21 and the outlet 22. Due to the above structure, the rotating body has a horizontal passage 31 and a vertical passage 33.

Thus, if the rotating body 30 is rotated, locations of the partitions 32a and 32b are changed so that a passage between the inlet 21 and the first entrance 23 is opened, or a passage between the outlet 22 and the first entrance 23 is opened by the horizontal passage 31 and the vertical passage 33, or a passage among the inlet 21, the outlet 22 and the first entrance 23 is blocked, the second entrance 24 is opened and a passage among the inlet 21, the outlet 22 and the first entrance 23 or a passage among the inlet 21, the outlet 22 and the second entrance 24 is simultaneously opened.

The connecting box 50 has a first passage 51 communicating the air outlet 12 of the air pressure generating unit 10 with the inlet 21 of the direction switching valve unit A and a second passage 52 communicating the air inlet 11 of the air pressure generating unit 10 with the outlet 22 of the direction switching valve unit A to form an air flow passage between the air pressure generating unit 10 and the direction switching valve unit A.

The case 60 is connected to the first entrance 23 of the direction switching valve unit A through a hose H and provided with a connecting port 70 connected to a mask hose (not shown) to be in contact with a mouth of a patient. The air pressure generating unit 10, the direction switching valve unit A and the connecting box 50 are mounted in the case 60, and the case has a coupling port 61 to which the connecting port 70 is coupled and a ventilation port 62 formed at a location corresponding to the second entrance 24 of the direction switching valve unit A.

By means of the above, the air which is forcedly caused to enter or forcedly discharged through the second entrance 24 of the direction switching valve unit A is forcedly caused to enter from or forcedly discharged to an outside through the ventilation port 62.

Due to the above structure, the conventional direction switching valve unit and the cough assisting device using the same are advantageous in that an external air can be suctioned or discharged forcedly through one entrance which is the second entrance 24 of the direction switching valve unit A.

In spite of the above advantages, however, the conventional direction switching valve and the cough assisting device using the same have the following drawbacks.

Firstly, in the rotating body 30 constituting the conventional direction switching valve and the cough assisting device using the same, since inflow and discharge of the air are controlled through the horizontal passage 31 and the vertical passage 33 formed by the pair of the partitions 32a and 32b, air flow paths of the horizontal passage 31 and the vertical passage 33 are lengthened and this problem causes an increase in a volume of the rotating body 30.

Due to the above, much electric power is consumed for rotating/driving the rotating body 30.

Secondly, in the conventional direction switching valve and the cough assisting device using the same, a cough noise coming from the second entrance 24 of the direction switching valve unit A according to a forcible discharge of the air is directly transmitted to an outside through the ventilation port 62 of the case 60, causing an extreme cough noise.

Thirdly, in the conventional direction switching valve and the cough assisting device using the same, the air forcedly discharged to an outside through the ventilation port 62 of the case 60 contains carbon dioxide and an odor causing substance produced in a patient's respiratory organ, and the forcedly discharged air stays in a space adjacent to the ventilation port 62 of the case 60.

However, since a patient forcedly inhales and exhales the air at least several times, there is a danger that the air which was forcedly discharged and stays in the space adjacent to the ventilation port 62 of the case 60 is forcedly inhaled into a patient's respiratory organ, and the greater the number of uses of the cough assisting device, the more serious this danger becomes.

Fourthly, a drawback of the conventional direction switching valve and the cough assisting device using the same is that amount of air which is forcedly suctioned is not adjusted in the preset air pressure.

In other words, it is possible to classify patients who need the cough assisting device into two groups. First, one group is routine patients who have healthy lungs or are not sensitive. In this case, although the time required for forcedly suctioning air in the preset air pressure is the same as that required for forcedly discharging air, it would not be a problem to induce a patient to cough.

The other group is specific patients who have weak lungs or are sensitive. In this case, however, as compared the time required for forcedly discharging air, much more time should be consumed to forcedly suction air in the preset air pressure (that is, an amount of the air which is forcedly suctioned per unit time should be less than amount of the air which is forcedly discharged per unit time) so that when a patient forcedly inhales the air, it is possible to induce a cough without serious damage to a patient's lung.

Because of this, there is a need to adjust an amount of air to be forcedly suctioned under a pressure preset according to a physical or mental condition of a patient.

SUMMARY OF THE INVENTION

The present invention is conceived for solving the drawbacks of the above conventional technology, and an object of the present invention is to provide a direction switching valve unit in which a passage formed in a rotating body for controlling inflow and discharge of air is subdivided into three (3) sub-passages to allow the air to enter and be discharged along the shortest paths so that the rotating body is miniaturized to reduce a driving electric power to be consumed for rotating/driving the miniaturized rotating body as compared with a conventional device, and the cough assisting device using the same.

Another object of the present invention is to provide a cough assisting device which guides the air forcedly discharged toward a patient's respiratory organ to allow the air to flow into the case body so that when a cough noise contained in the air forcedly discharged from a patient's respiratory organ collides with the case body, some of the cough noise is damped and then penetrates the case body and the remainder of the cough noise of a patient, which does not penetrate the case body, is reflected and dispersed in the case body or damped and penetrates the case body again to minimize the cough noise and to minimize reabsorption of carbon dioxide and an odor causing substance contained in a cough of patient into air supplied from an outside when the device is repeatedly utilized for inducing a patient to cough.

Still another object of the present invention is to provide a cough assisting device provided with a means for adjusting amount of air which is forcedly suctioned under a preset air pressure.

As the technical spirit for achieving the present invention, the direction switching valve unit of the present invention includes a housing having a receiving space formed near a central part of an upper surface thereof; a first vertical passage formed for communicating an outside of a lower surface with the receiving space; a second vertical passage formed for communicating the receiving space with an outside of one side surface; a first horizontal passage formed for communicating the receiving space with one side part of the upper surface; a second horizontal passage formed for communicating the receiving space with an outside of the other side surface; and a third horizontal passage formed for communicating the first vertical passage with an opened portion of the upper surface; a receiving body fixed in the receiving space of the housing and having communication ports formed at and penetrating locations corresponding to four (4) opened portions of the receiving space; a rotating body placed on the receiving body, the rotating body having an upper plate, a lower plate and first and second partitions connecting the upper plate and the lower plate to form a first direct passage, a second direct passage and a third direct passage, both sides of each of the direct passages being opened; and a two-directional motor provided at an upper side of the housing and connected to a shaft of the rotating body.

A cough assisting device using the direction switching valve unit according to the present invention includes a case body having an inhaling space formed on and passing through a lower surface thereof; an air pressure generating unit provided in the case body, the air pressure generating unit generating an air pressure through a rotation force for suctioning air into an air inlet and discharging suctioned air via an air outlet; and a direction switching valve unit provided in the inhaling space formed in the case body, the direction switching valve unit converting a flow direction of the air for forcedly suctioning air toward a patient's respiratory organ or forcedly discharging air from a patient's respiratory organ by means of air pressure generated in the air pressure generating unit.

BRIEF DESCRIPTION OF THE DRAWINGS

The above and other objects, features and advantages of the present invention will become more apparent to those of ordinary skill in the art by describing in detail example embodiments thereof with reference to the attached drawings, in which:

FIG. 14A shows a combination of sensor/disc and a sectional view of a direction switching valve unit taken along line C-C in FIG. 7 and FIG. 14B shows a sectional view taken along line D-D in FIG. 7;

FIG. 16A shows a combination of sensor/disc and a sectional view of a direction switching valve unit taken along line C-C in FIG. 7 and FIG. 16B shows a sectional view taken along line D-D in FIG. 7;

FIG. 17A shows a combination of sensor/disc and a sectional view of a direction switching valve unit taken along line C-C in FIG. 7 and FIG. 17B shows a sectional view taken along line D-D in FIG. 7;

DETAILED DESCRIPTION OF EXAMPLE EMBODIMENTS

Hereinafter, an example embodiment of the present invention will be described in detail with reference to the accompanying drawings.

Figure 1:
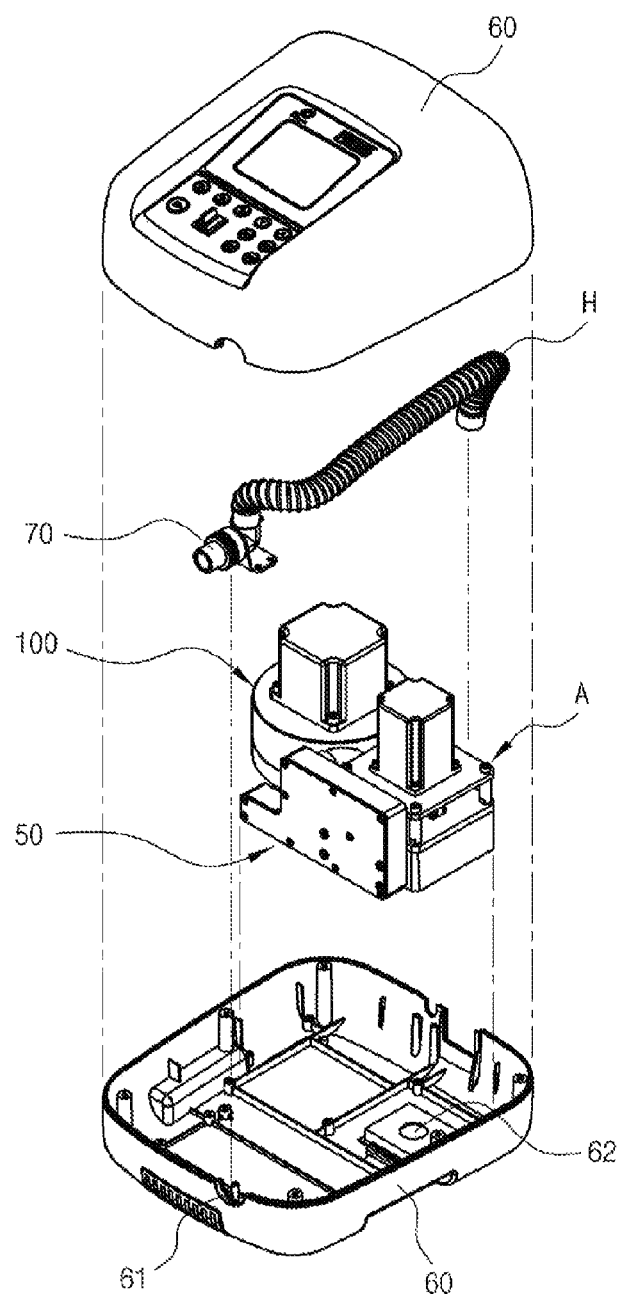
FIG. 1 is an exploded perspective view of a conventional direction switching valve unit and a cough assisting device using the same.
Figure 2:
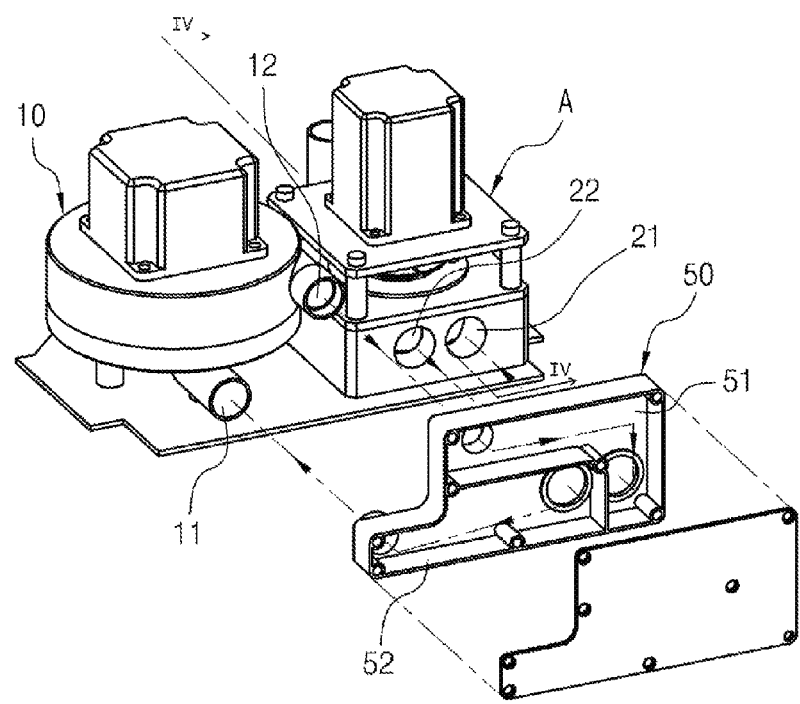
FIG. 2 is an essential perspective view showing an air pressure generating unit, a direction switching valve unit and a connecting box constituting the conventional direction switching valve unit and the cough assisting device using the same.
Figure 3:
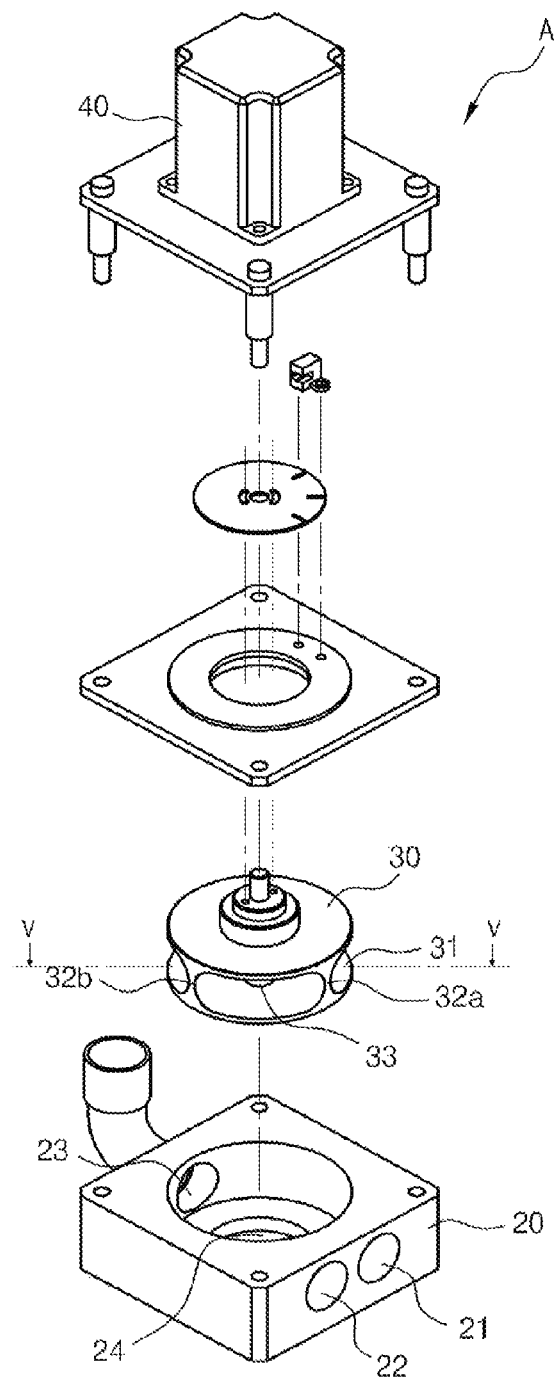
FIG. 3 is an exploded perspective view showing the direction switching valve unit constituting the conventional direction switching valve unit and the cough assisting device using the same.
Figure 4:
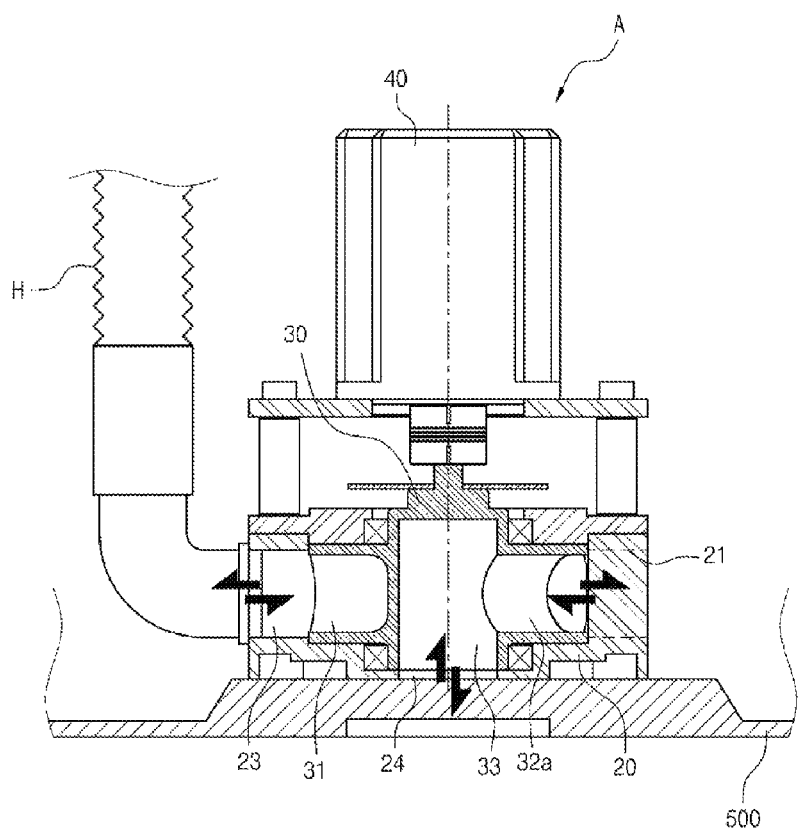
FIG. 4 is a sectional view taken along line IV-IV in FIG. 2, showing a coupling state of the air pressure generating unit, the direction switching valve unit and the connecting box constituting the conventional direction switching valve unit and the cough assisting device using the same.
Figure 5:
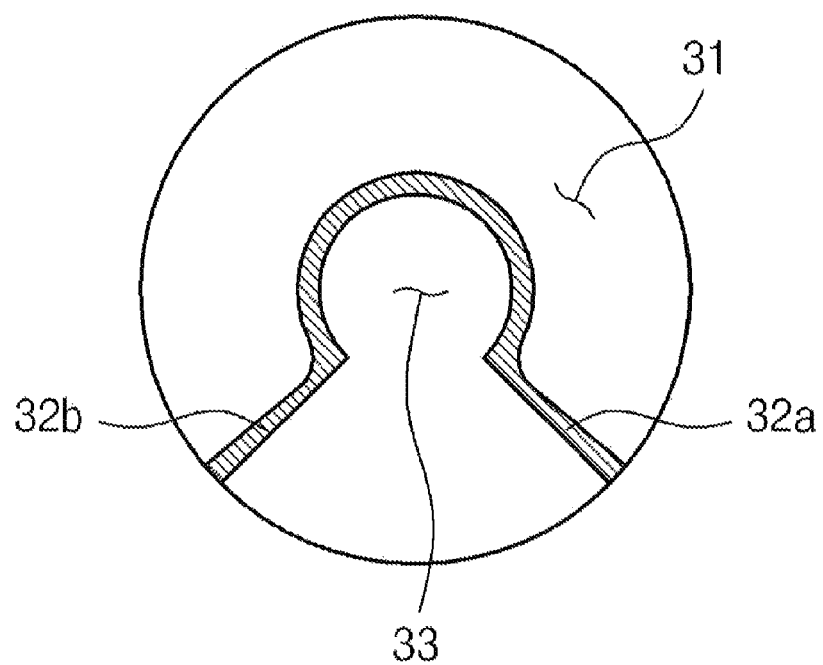
FIG. 5 is a sectional view taken along line V-V in FIG. 3, showing a rotating body included in the air pressure generating unit and the direction switching valve unit constituting the conventional direction switching valve unit and the cough assisting device using the same.
Figure 6:
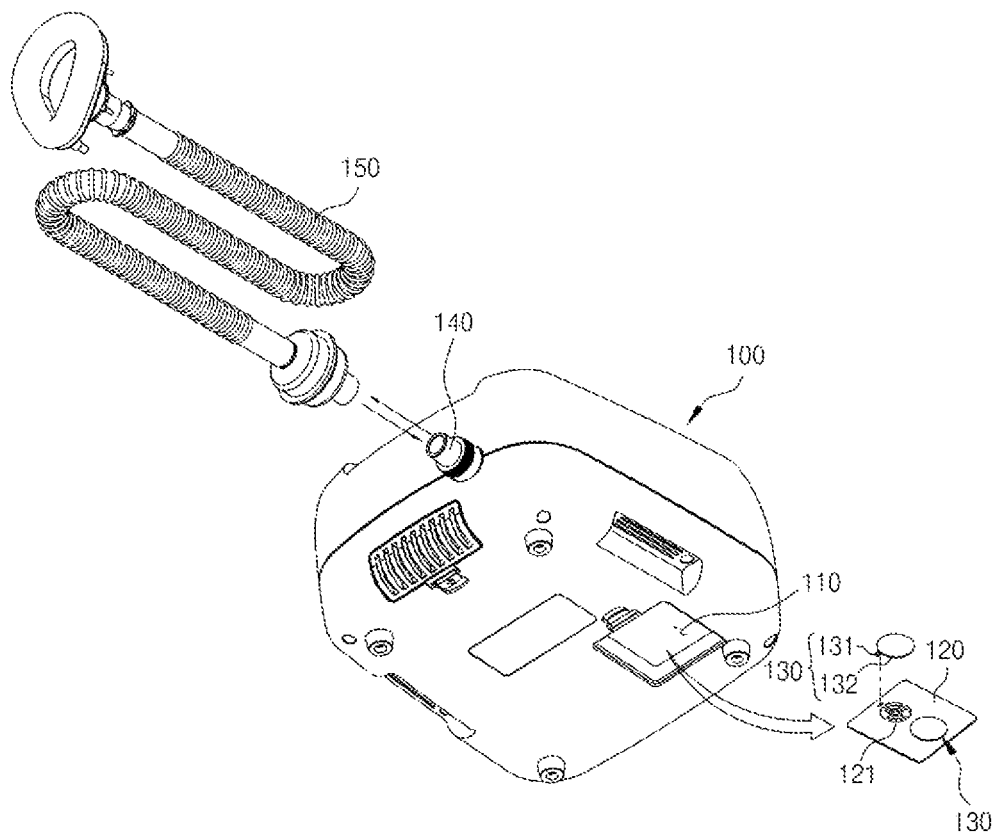
FIG. 6 is a bottom perspective view of a cough assisting device according to the present invention.
Figure 7:
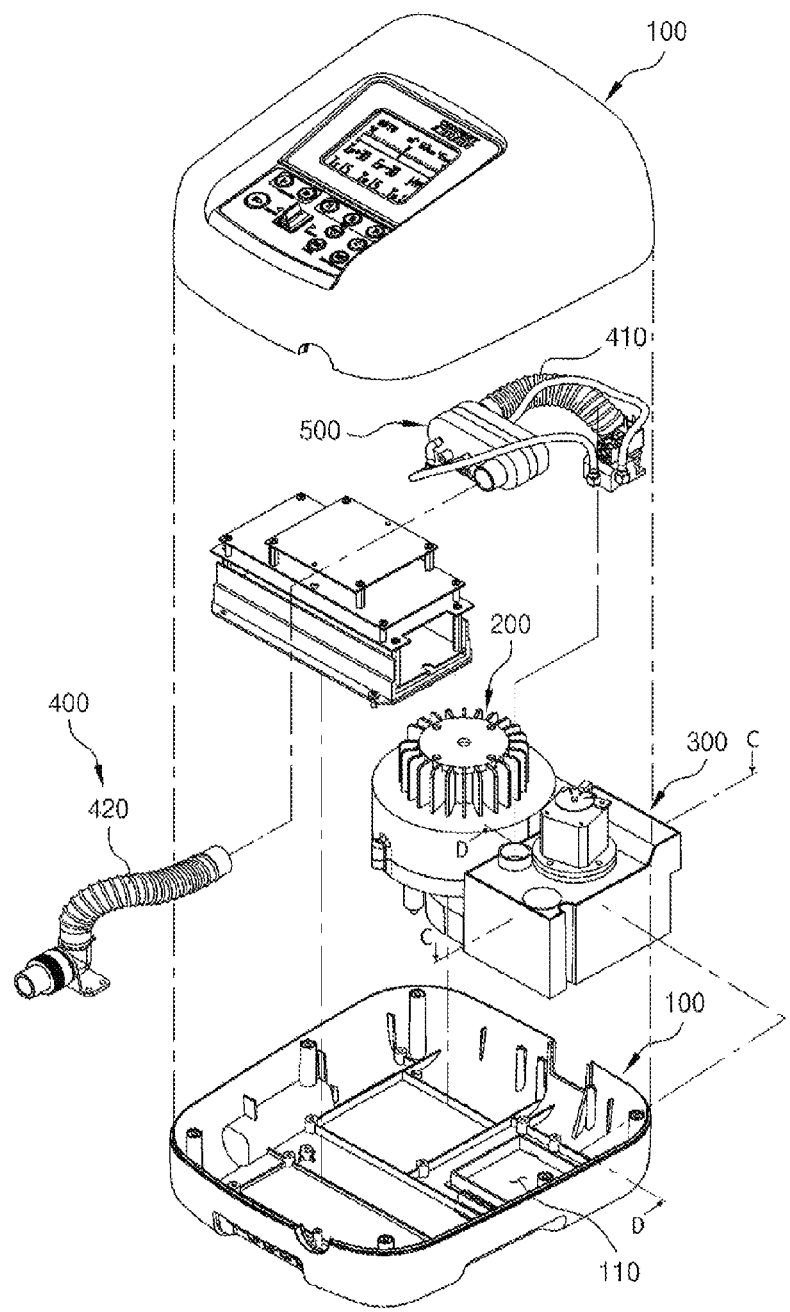
FIG. 7 is an exploded perspective view illustrating an internal structure of the cough assisting device according to the present invention.
Figure 8:
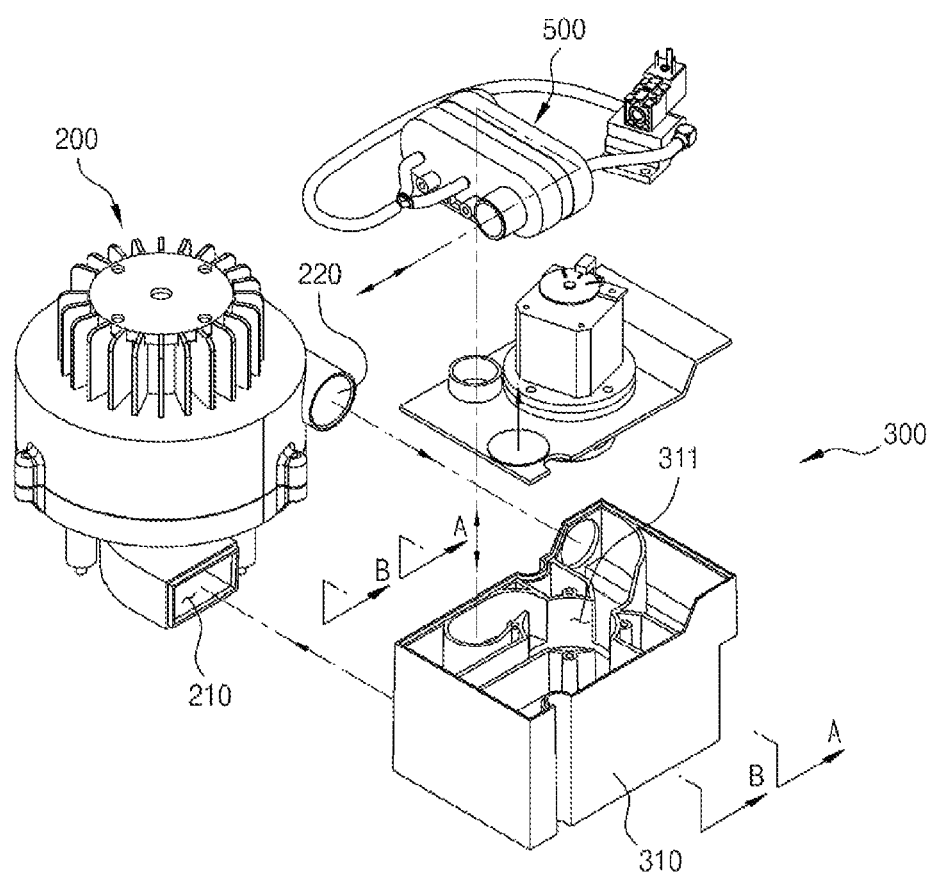
FIG. 8 is an essential perspective view showing an air pressure generating unit, a direction switching valve unit and the like constituting the cough assisting device according to the present invention.
Figure 9:
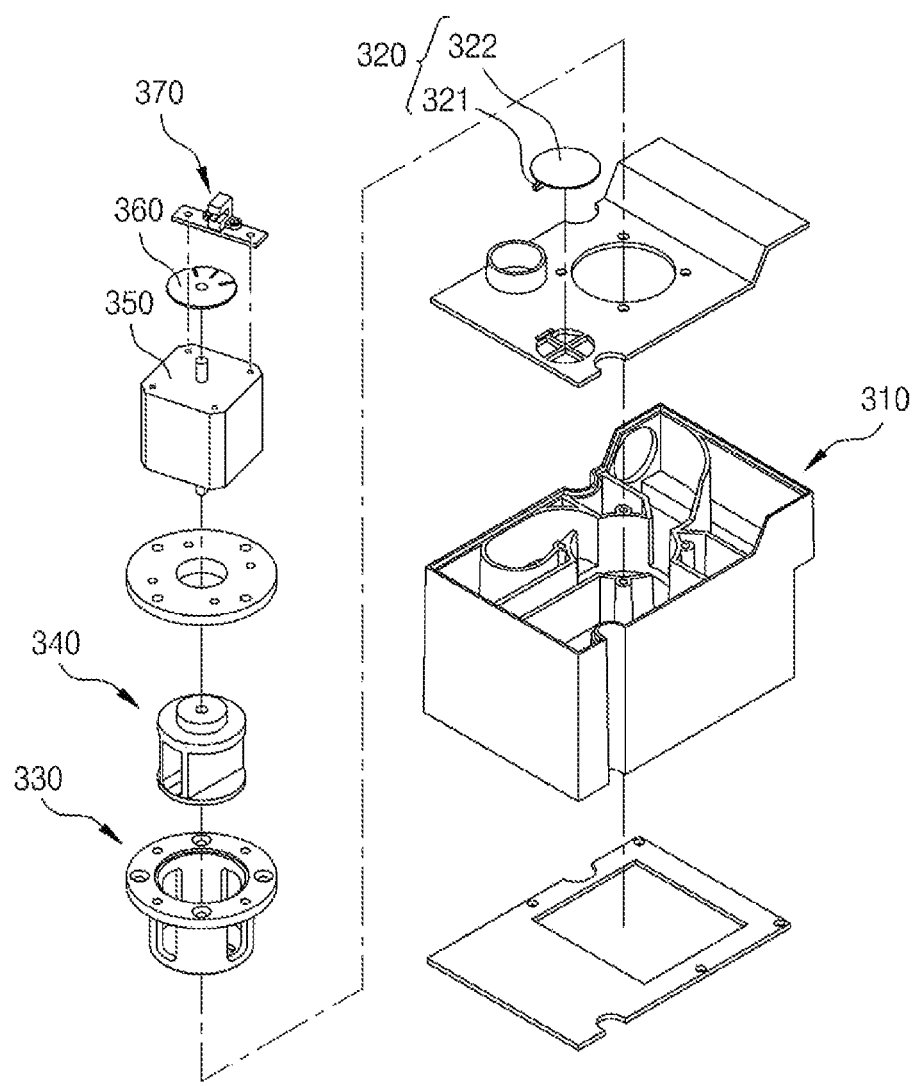
FIG. 9 is an essential perspective view showing the direction switching valve unit constituting the cough assisting device according to the present invention.
Figure 10:
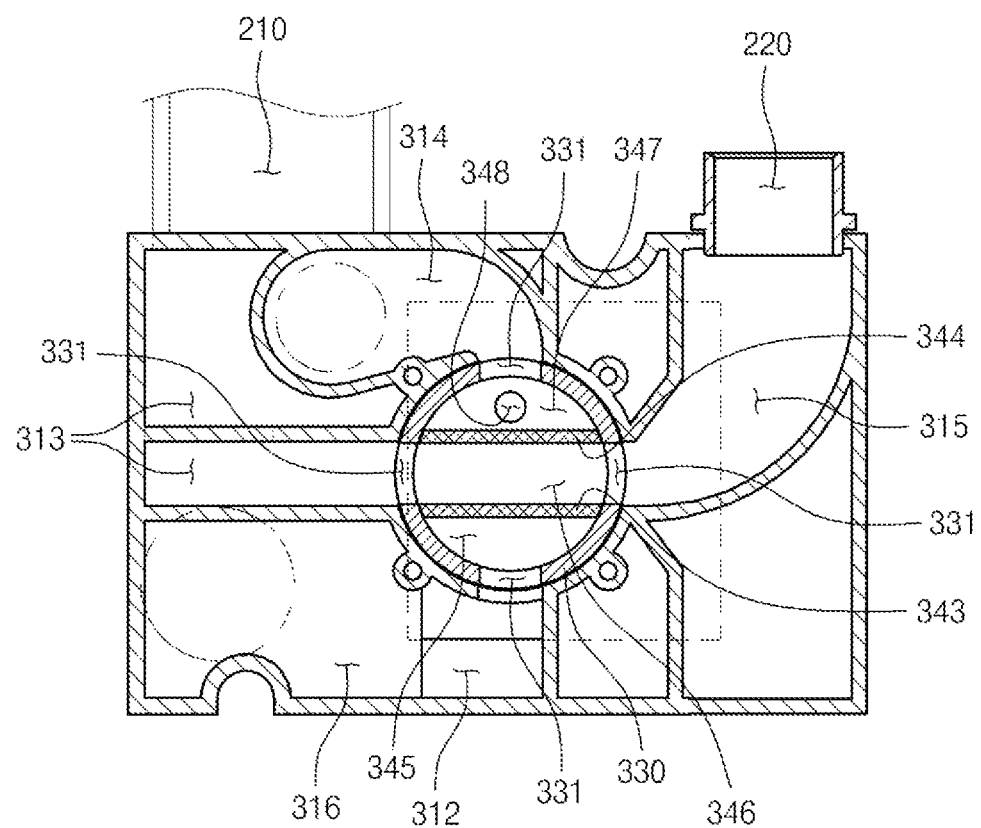
FIG. 10 is a cross-sectional view taken along line C-C in FIG. 7, showing a coupling state of the direction switching valve unit constituting the cough assisting device according to the present invention.
Figure 11:
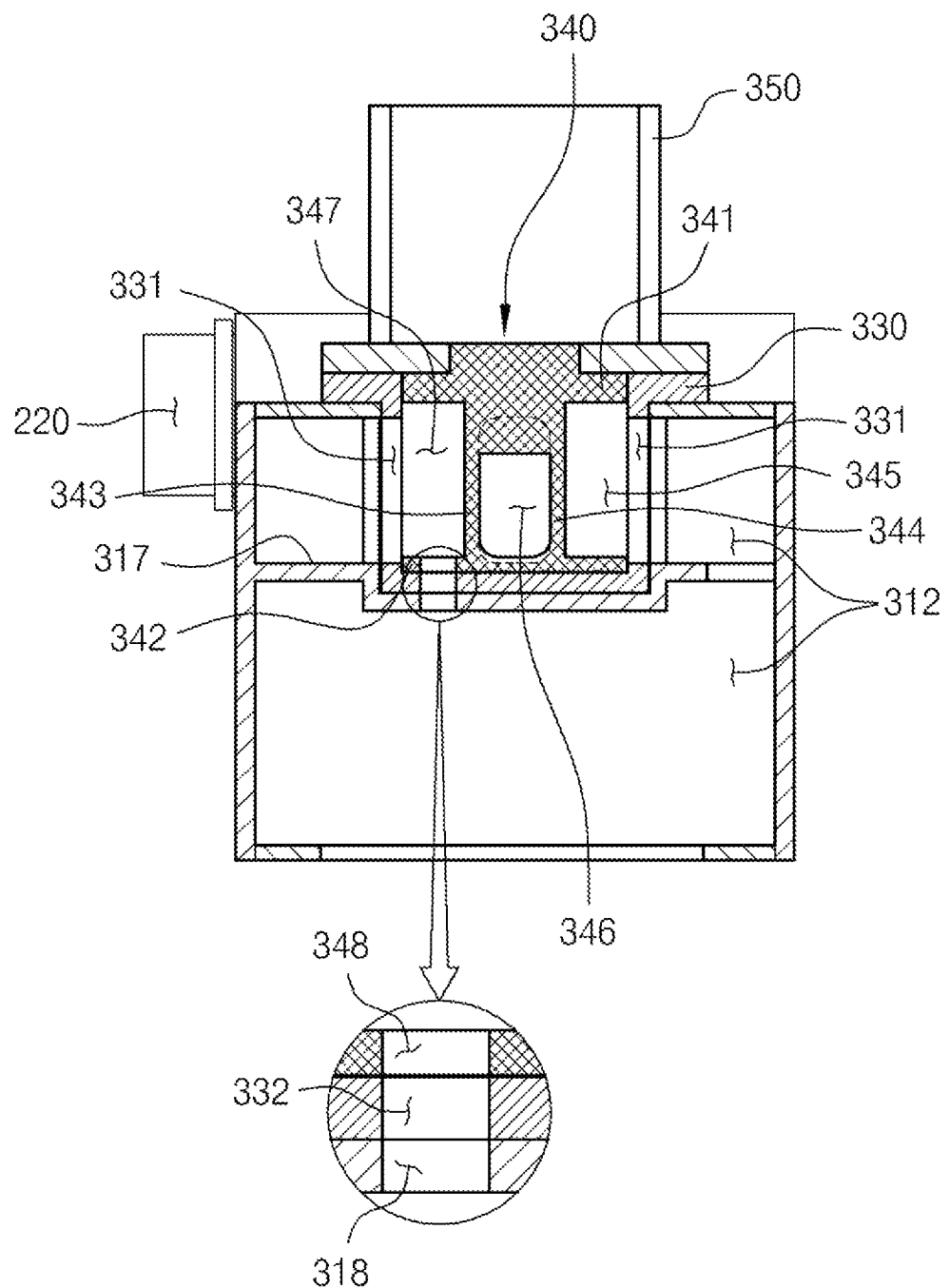
FIG. 11 is a sectional view taken along the line A-A in FIG. 8 of the direction switching valve unit constituting the cough assisting device according to the present invention.
Figure 12:
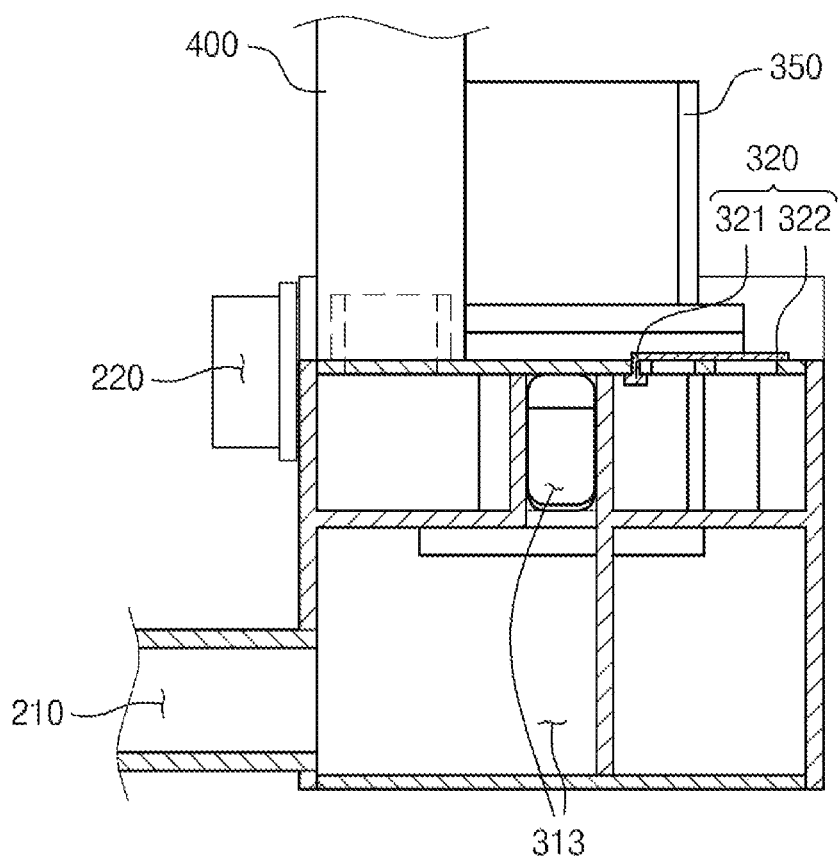
FIG. 12 is a sectional view taken along the line B-B in FIG. 8 of the direction switching valve unit constituting the cough assisting device according to the present invention.
Figure 13:
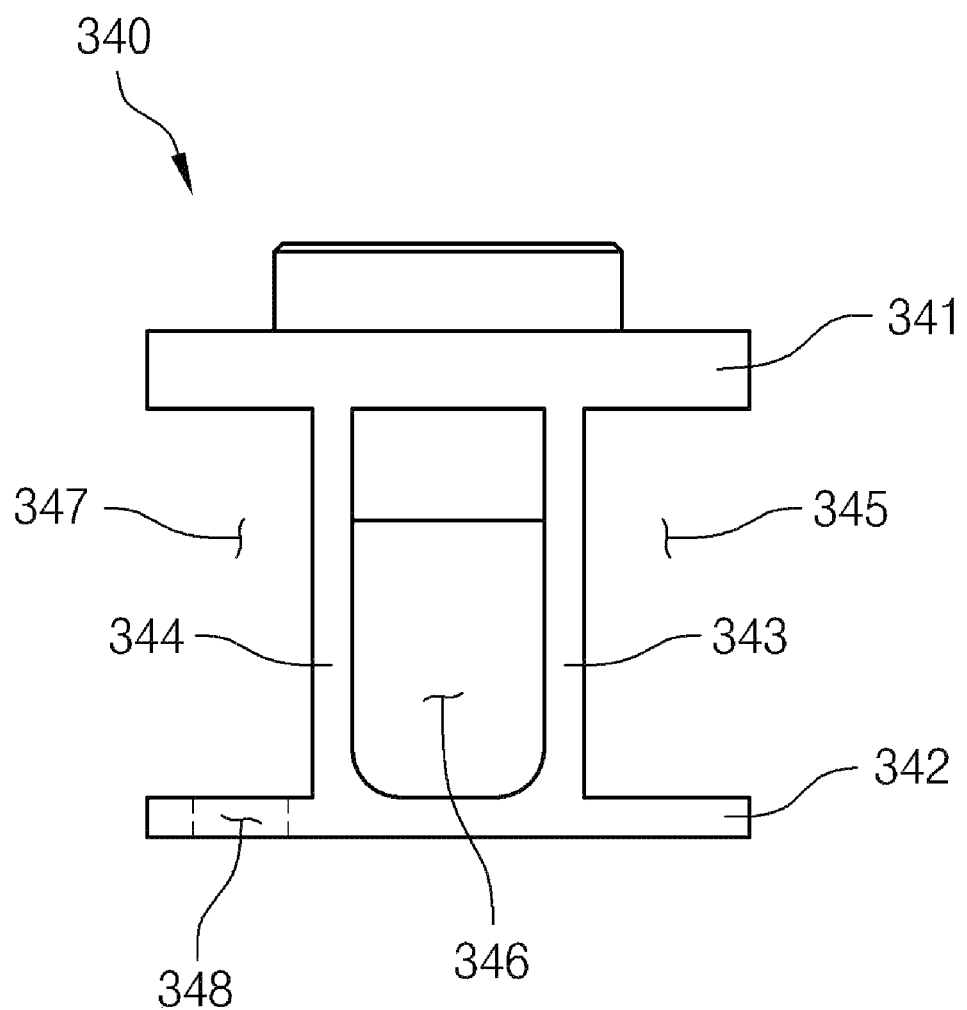
FIG. 13 is a side view of a rotating body constituting the cough assisting device according to the present invention.
Figure 14A:
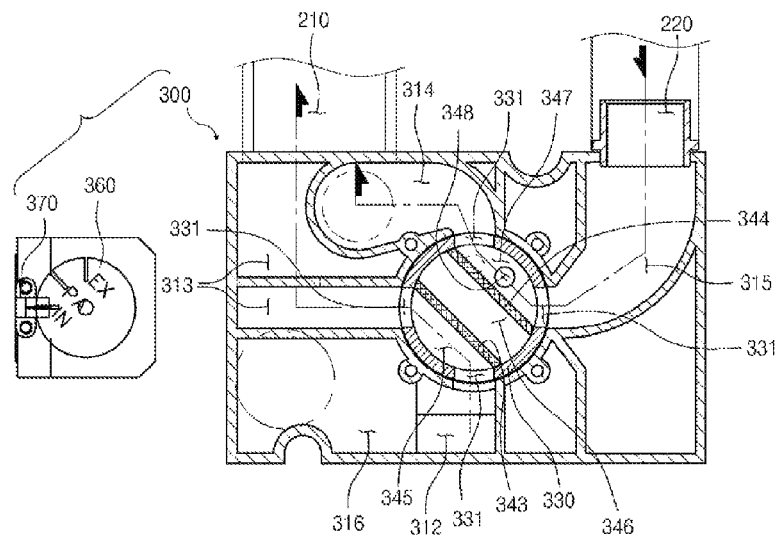
FIGS. 14A and 14B illustrate a state in use of the cough assisting device according to the present invention which is operated in the inhale mode.
Figure 14B:
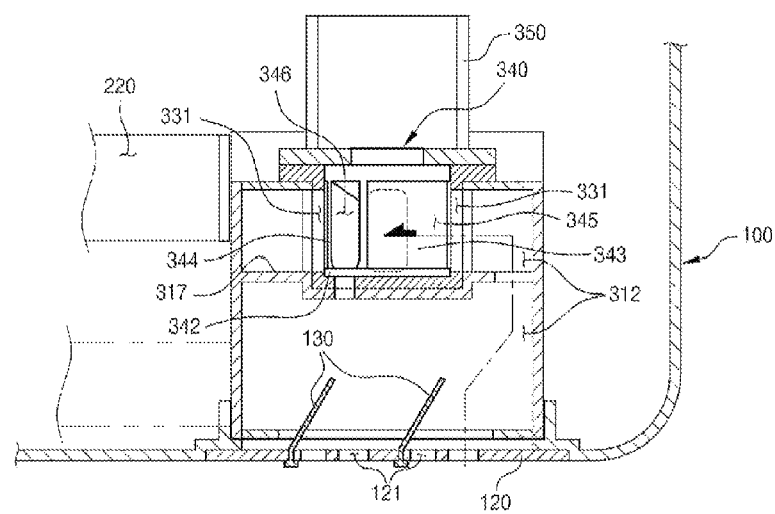
Figure 15:
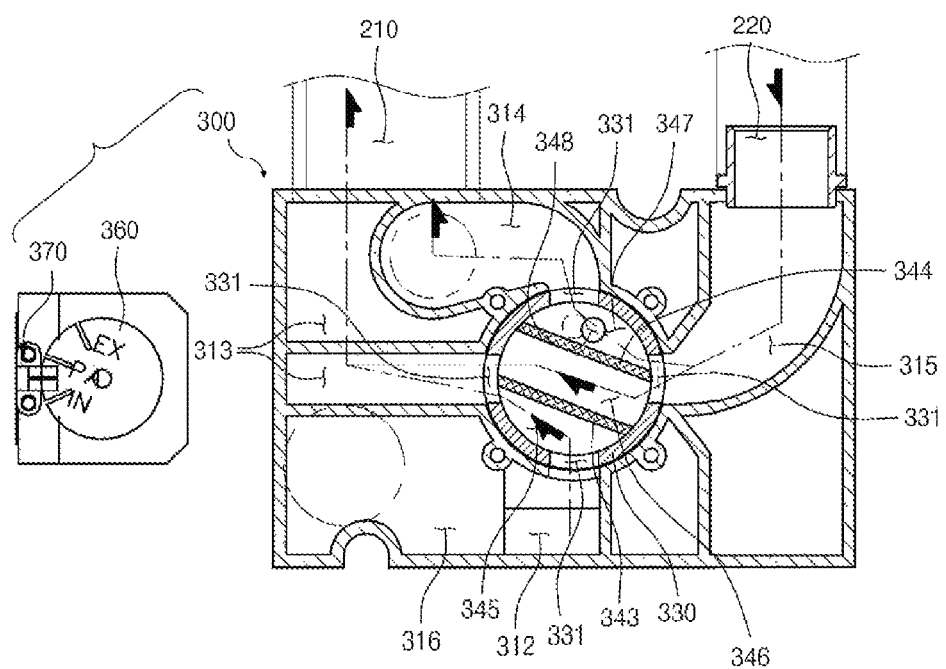
FIG. 15 illustrate a state in use of the cough assisting device according to the present invention which is operated in the half-inhale mode, and shows a combination of sensor/disc and a sectional view of a direction switching valve unit taken along line C-C in FIG. 7.
Figure 16A:
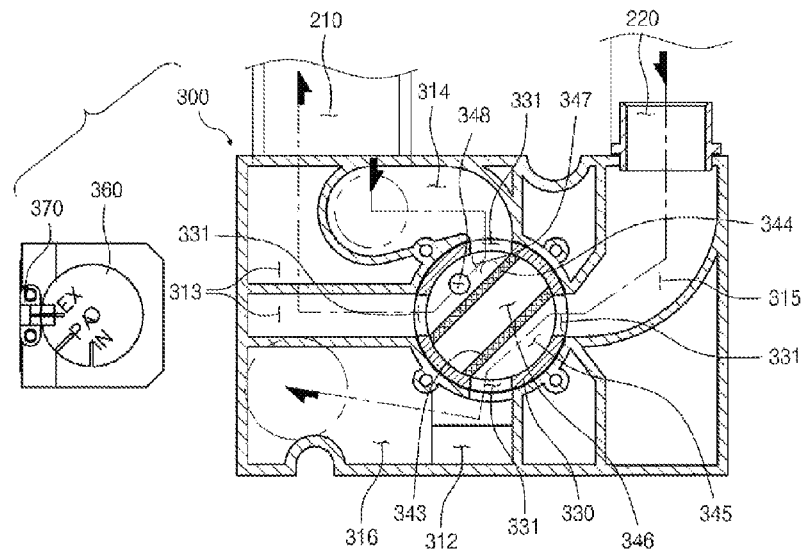
FIGS. 16A and 16B illustrate a state in use of the cough assisting device according to the present invention which is operated in the exhale mode.
Figure 16B:
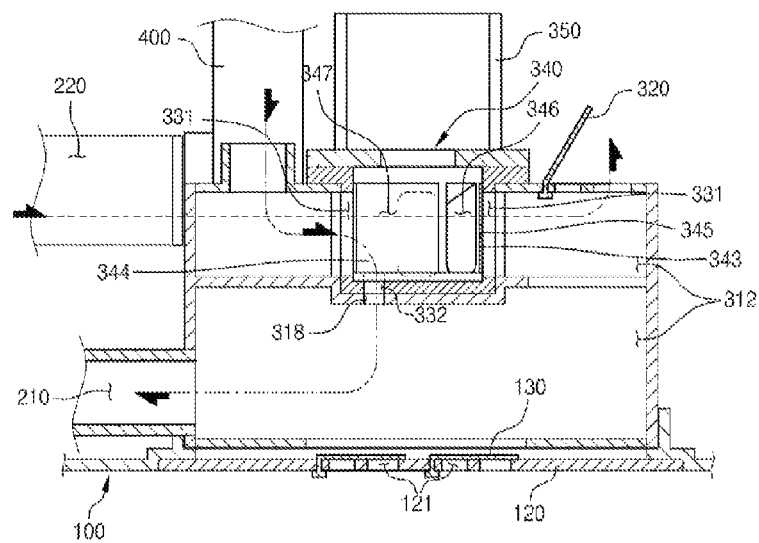
Figure 17A:
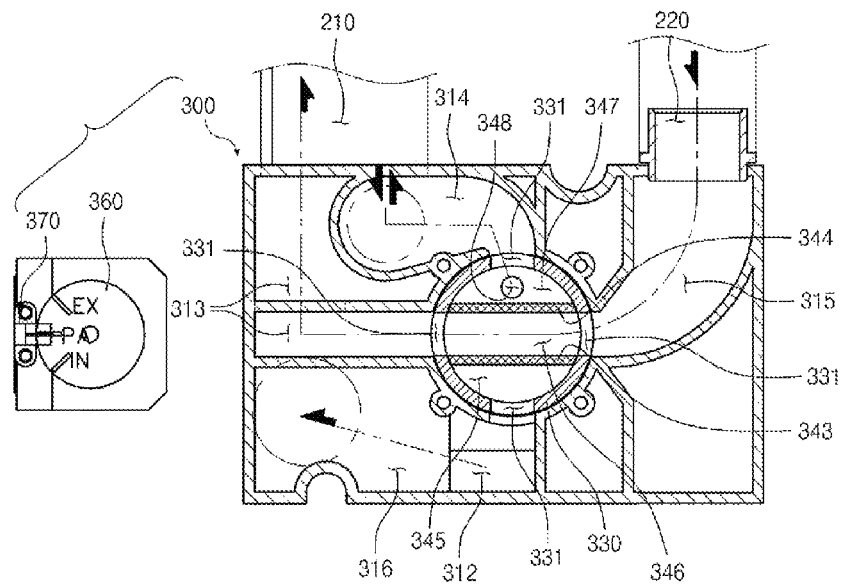
FIGS. 17A and 17B illustrate a state in use of the cough assisting device according to the present invention which is operated in the pause mode.
Figure 17B:
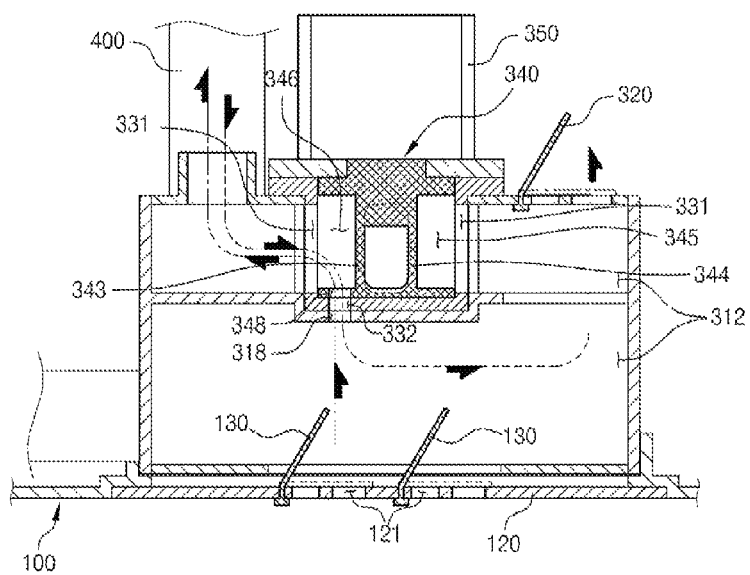
Figure 18:
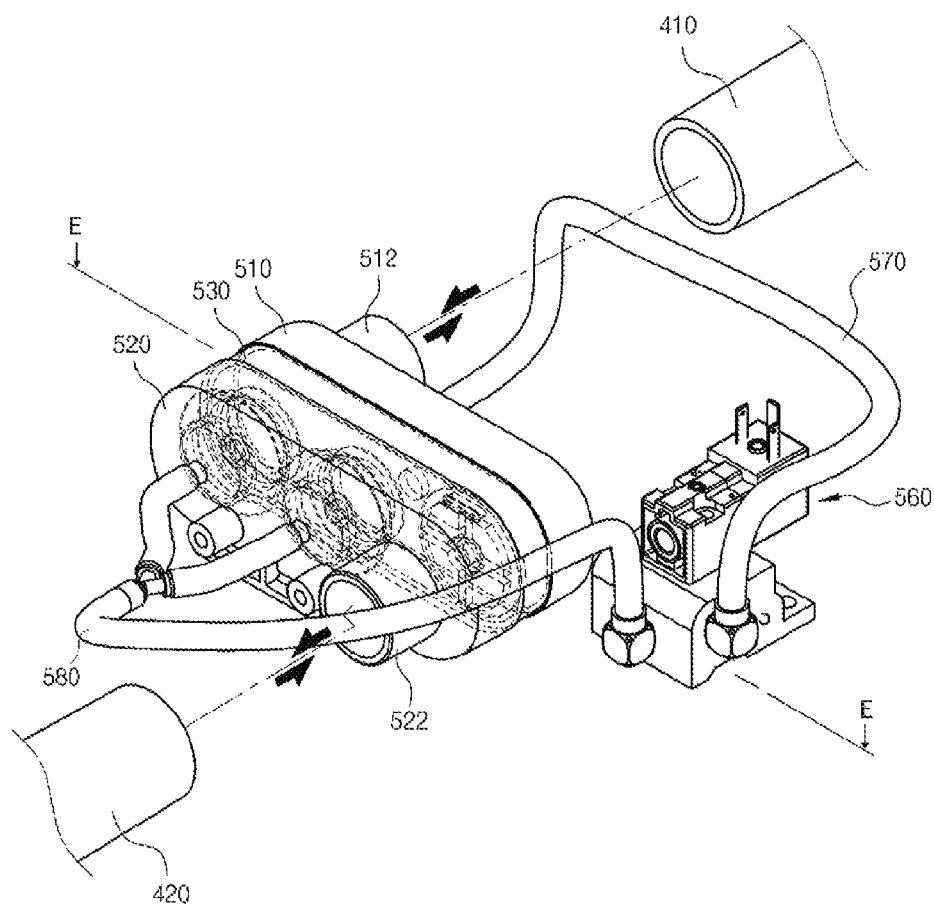
FIG. 18 is an external perspective view of an air-inflow rate adjusting means constituting the cough assisting device according to the present invention.
Figure 19:
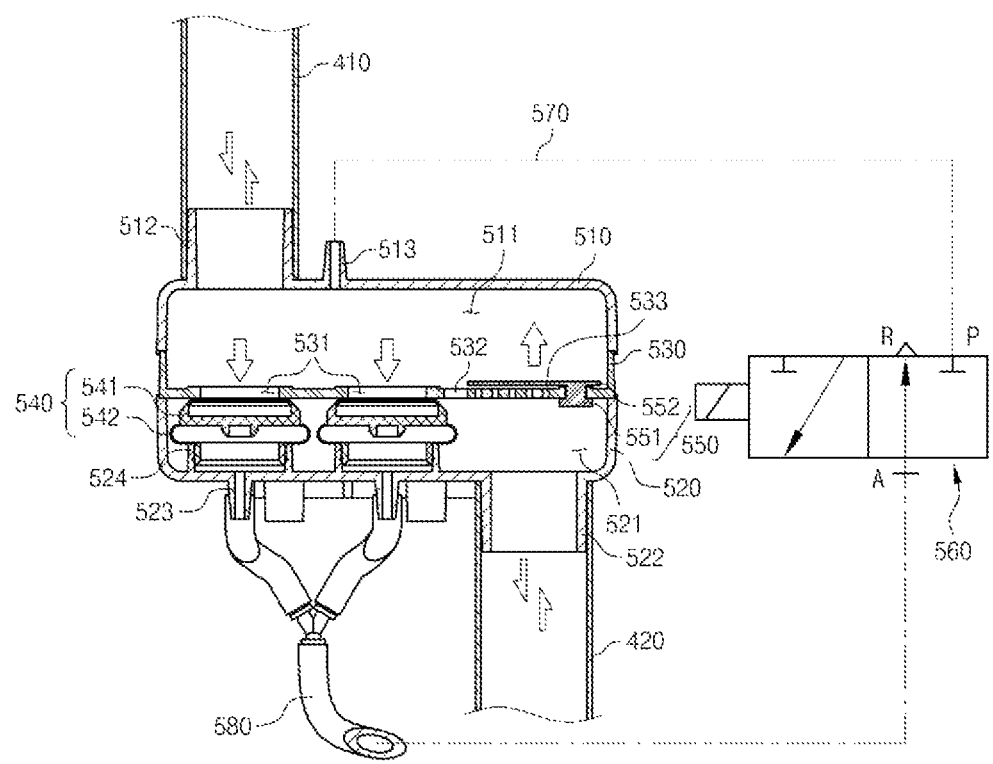
FIG. 19 is a sectional view taken along line E-E in FIG. 18 of the air-inflow rate adjusting means constituting the cough assisting device according to the present invention.
Figure 20:
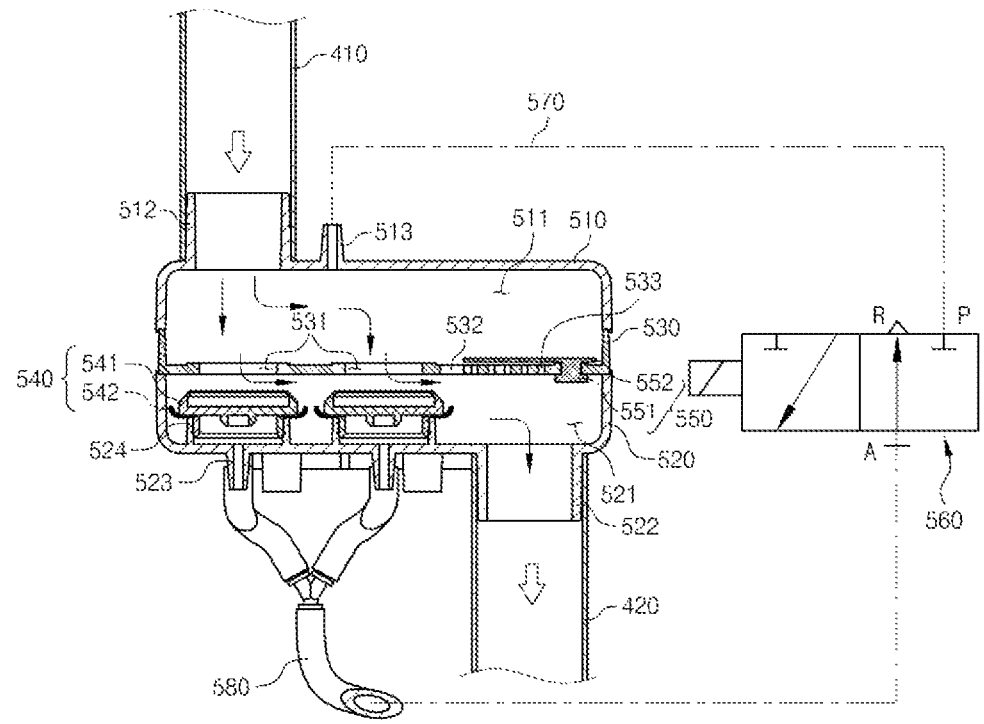
FIG. 20 and FIG. 21 are sectional views taken along line E-E in FIG. 18, illustrating a state in use of the cough assisting device according to the present invention which is operated in the inhale mode and the exhale mode by operation of the air-inflow rate adjusting means provided in the cough assisting device of the present invention in order to induce a routine patient having healthy lungs or who is not sensitive to cough.
Figure 21:
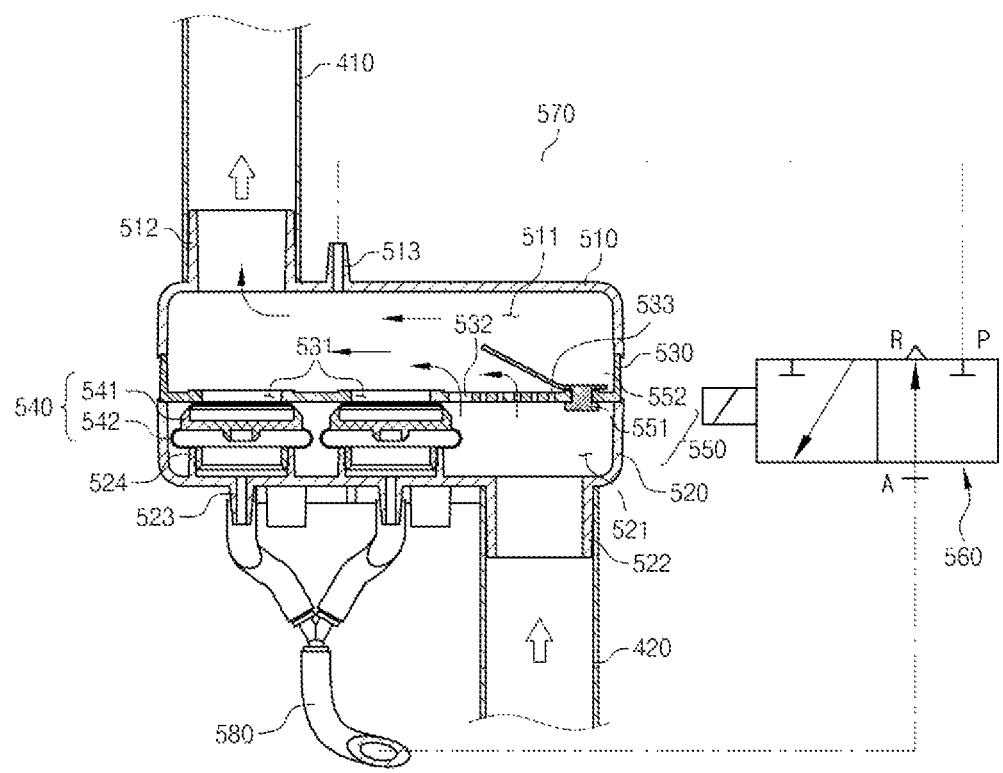
Figure 22:
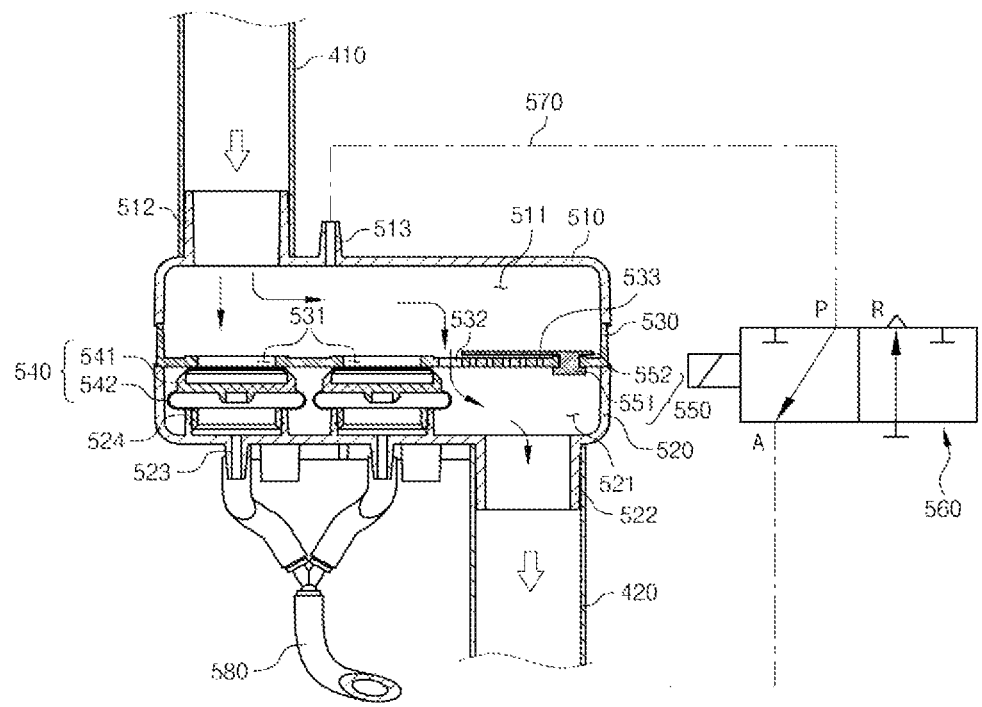
FIG. 22 and FIG. 23 are sectional views taken along line E-E in FIG. 18, illustrating a state in use of the cough assisting device according to the present invention which is operated in the inhale mode and the exhale mode by operation of the air-inflow rate adjusting means provided in the cough assisting device of the present invention in order to induce a specific patient having weak lungs or who is sensitive to cough.
Figure 23:
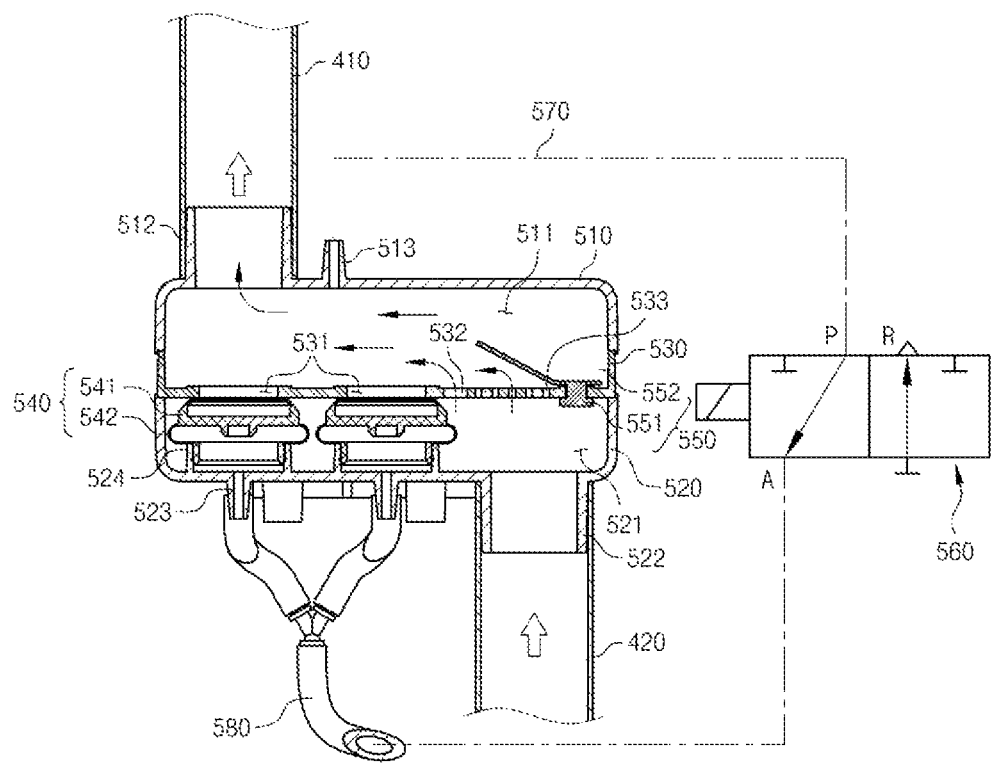

FIG. 6 is a bottom perspective view of a cough assisting device according to the present invention; FIG. 7 is an exploded perspective view illustrating an internal structure of the cough assisting device according to the present invention; FIG. 8 is an essential perspective view showing an air pressure generating unit, a direction switching valve unit and the like constituting the cough assisting device according to the present invention; FIG. 9 is an essential perspective view showing the direction switching valve unit constituting the cough assisting device according to the present invention; FIG. 10 is a cross-sectional view showing a coupling state of the direction switching valve unit constituting the cough assisting device according to the present invention; FIG. 11 is a sectional view taken along the line A-A of the direction switching valve unit constituting the cough assisting device according to the present invention; FIG. 12 is a sectional view taken along the line B-B of the direction switching valve unit constituting the cough assisting device according to the present invention; FIG. 13 is a side view of a rotating body constituting the cough assisting device according to the present invention; FIGS. 14A and 14B are views illustrating a state in use of the cough assisting device according to the present invention which is operated in the inhale mode; FIG. 15 is a view illustrating a state in use of the cough assisting device according to the present invention which is operated in the half-inhale mode; FIGS. 16A and 16B are views illustrating a state in use of the cough assisting device according to the present invention which is operated in the exhale mode; FIGS. 17A and 17B are views illustrating a state in use of the cough assisting device according to the present invention which is operated in the pause mode; FIG. 18 is an external perspective view of an air-inflow rate adjusting means constituting the cough assisting device according to the present invention; FIG. 19 is a sectional view of the air-inflow rate adjusting means constituting the cough assisting device according to the present invention; FIG. 20 and FIG. 21 are views illustrating a state in use of the cough assisting device according to the present invention which is operated in the inhale mode and the exhale mode by operation of the air-inflow rate adjusting means provided in the cough assisting device of the present invention in order to induce a routine patient, who has a healthy lung or is not sensitive, to cough; and FIG. 22 and FIG. 23 are views illustrating a state in use of the cough assisting device according to the present invention which is operated in the inhale mode and the exhale mode by operation of the air-inflow rate adjusting means provided in the cough assisting device of the present invention in order to induce a specific patient, who has a weak lung or is sensitive, to cough.

As shown in the drawings, the cough assisting device of the present invention mainly consists of a case body 100, an air pressure generating unit 200 and a direction switching valve unit 300.

First, the case body 100 is an external member to which all kinds of structural elements including the air pressure generating unit 200 and the direction switching valve unit 300 (described below) which are necessary for operating the cough assisting device are mounted, an inhaling space 110 is formed on and passes through a lower surface of the case body, and a closing plate 120 on which an opening 121 is formed is detachably attached to the case body to close the inhaling space 110.

Here, the opening 121 is formed on the closing plate 120 to enable external fresh air to be supplied to a patient.

At this time, a one-way valve part 130 for the case body is mounted in the opening 121 of the closing plate 120, and the one-way valve part for the case body is controlled to allow external air to enter a first vertical passage 312 included in the direction switching valve unit 300 and to prevent air in the case body 100 from being discharged through the opening 121, so that when the device according to the present invention is repeatedly utilized for inducing a patient to cough, the one-way valve part minimizes reabsorption of carbon dioxide and an odor causing substance contained in a cough of the patient into air supplied from an outside.

The one-way valve part 130 for the case body performing the above function is formed of an elastic material, the one-way valve part 130 may consist of a rubber plate 132, one side of which can be fixedly mounted to an upper surface of the closing plate 120, which is placed in the case body 100, through a fixing protrusion 131 to open the opening 121 by means of air pressure.

In addition, a connecting port 140 is provided on the case body 100, the connecting port passes through the case body 100 and communicates with a mask hose 150 through one side thereof. A relaying hose 400 is provided in the case body 100, one end of which communicates with the other side of the connecting port 140 and the other end of which being communicates with the direction switching valve unit 300 to be described below. Thus, an air flow passage through which air can be forcedly supplied to a patient or forcedly discharged is provided.

The air pressure generating unit 200 is mounted in the case body 100 and is the member generating an air pressure through a turbo fan operated by a rotational force of a motor, suctioning air into an air inlet 210 and discharging suctioned air via an air outlet 220. According to one embodiment of the air pressure generating unit 200 performing the above function, the air inlet 210 and the air outlet 220 may be disposed toward a front.

The direction switching valve unit 300 is provided in the inhaling space 110 formed in the case body 100, and converts a flow direction of the air for forcedly suctioning air toward a patient's respiratory organ or forcedly discharging air from a patient's respiratory organ by means of air pressure generated in the air pressure generating unit 200. The direction switching valve unit 300 guides an air flow direction along the shortest path and may adjust an air pressure during a forcible suction and a forcible discharge to adjust an amount of air entering and being discharged according to a patient's condition This direction switching valve unit 300 performing the above function consists of a housing 310, a one-way valve part 320 for the housing, a receiving body 330, a rotating body 340, a two-directional motor 350, and the like.

First, the housing 310 is installed in the inhaling space 110 formed on and passing through the case body 100. In the housing, a receiving space 311 is formed on an upper surface through a plurality of vertical partitions, the first vertical passage 312 communicating the inhaling space 110 and the receiving space 311 is formed, a second vertical passage 313 communicating the receiving space 311 and the air inlet 210 of the air pressure generating unit 200 is formed, a first horizontal passage 314 communicating the receiving space 311 and the relaying hose 400 is formed, a second horizontal passage 315 communicating the receiving space 311 and the air outlet 220 of the air pressure generating unit 200 is formed, and a third horizontal passage 316 communicating the vertical passage 312 and an opened portion of the upper surface is formed.

According to a rotation of the rotating body 340 which will be described later, in this structure, the first vertical passage 312, the second vertical passage 313, the first horizontal passage 314, the second horizontal passage 315 and the first vertical passage 312 communicate with each other or are isolated from each other to form various air flow passages.

In addition, a horizontal partition 317 is provided in the housing 310 to enable the receiving body 330 described below to be secured to the horizontal partition 317 in the state in which the receiving body 330 is laid on the horizontal partition 317.

The one-way valve part 320 for the housing is a member provided for opening/closing an opened portion of the third horizontal passage 316 of the housing 310 to allow air in the third horizontal passage 316 to be discharged only to an outside.

Through the above function, the one-way valve part 320 for the housing guides the air, which is discharged through the relaying hose 400 to be described below, discharged forcedly from a patient's respiratory organ to allow this air to flow into the case body 100 so that when a cough noise contained in the air forcedly discharged from a patient's respiratory organ collides with an inside of the case body 100, some of the cough noise is damped and then penetrates the case body 100, and the remainder of the cough noise of the patient, which does not penetrate the case body, is reflected and dispersed in the case body 100 or damped and penetrates the case body 100 again to minimize the cough noise and to minimize reabsorption of carbon dioxide and an odor causing substance contained in a cough of the patient into air supplied from an outside when the device is repeatedly utilized for inducing the patient to cough.

The one-way valve part 320 for the housing performing the above function is formed of an elastic material which is the same as that of the one-way valve part 130 for the case body mentioned above, and this one-way valve part 320 for the housing may consist of a rubber plate 322, one side of which can be fixedly mounted to an upper surface of the housing 310, which is placed outside of the housing 310, through a fixing protrusion 321 to open the opening portion by means of air pressure.

The receiving body 330 is placed in and secured to the receiving space 311 of the housing 310 to allow the rotating body 340 to be described below to be rotated and to allow the first vertical passage 312, the second vertical passage 313, the first horizontal passage 314, the second horizontal passage 315 and the first vertical passage 312 of the housing 310 and the rotating body 340 to communicate with each other.

The rotating body 340 is placed on the receiving body 330 and is provided with an upper plate 341, a lower plate 342 and first and second partitions 343 and 344 communicating the upper plate 341 with the lower plate 342 to form a first direct passage 345, a second direct passage 346 and a third direct passage 347 in the rotating body. Here, both sides of each of the direct passages are opened.

By the above, the rotating body 340 has a structure which guides the air to enable the air to flow linearly without bypassing when air flows through the first vertical passage 312, the second vertical passage 313, the first horizontal passage 314, the second horizontal passage 315 and the first vertical passage 312 of the housing 310 according to a rotation of the rotating body 340.

Because of this, it is possible to minimize a volume of the rotating body 340 so that, as compared with a conventional device, less driving power required for rotating/driving the minimized rotating body 340 is consumed.

Among the members constituting the rotating body 340, the lower plate 342 on which the third direct passage 347 is formed has an upper hole 348 for normal respiration formed thereon, a relaying hole 332 for normal respiration, corresponding to the upper hole 348 for normal respiration of the rotating body 340, is formed on a bottom surface of the receiving body 330, and a lower hole 318 for normal respiration, corresponding to the relaying hole 332 for normal respiration of the receiving body 330, is formed on the horizontal partition 317, whereby the device is controlled such that the upper hole 348 for normal respiration, the relaying hole 332 for normal respiration and the lower hole 318 for normal respiration overlap each other in the pause mode to enable the patient to breathe normally.

The two-directional motor 350 is provided at an upper side of the housing 310 and fixed to a shaft of the rotating body 340 to adjust a rotation direction and a rotating angle of the rotating body 340.

In addition, the air pressure generating unit 200 includes a sensing means for sensing rotation of the rotating body 340 and controlling driving of the two-directional motor 350.

In other words, the user/patient can recognize a degree of pressure of air supplied or suctioned through the relaying hose 400 through a current rotating angle of the rotating body 340 sensed by the sensing means and adjust an accurate air pressure on the basis of air pressure.

As one embodiment, the above sensing means includes a disc 360 coupled to an upper shaft of the two-directional motor 350 and having marks formed along an edge thereof at regular intervals and a sensor 370 provided at an upper side of the two-directional motor 350 for sensing the marks of the disc 360.

Here, holes which can be sensed by a sensor can be employed as the marks of the disc 360, in which case a photo sensor utilizing an optical signal can be utilized as the sensor 370.

The process for inducing a cough through the cough assisting device constructed as above is performed in the inhale mode (including the half-inhale mode), the exhale mode and the pause mode which form one cycle. The process for inducing a cough is illustrated with reference to FIGS. 14A and 14B to FIGS. 17A and 17B.

Referring to FIGS. 14A and 14B, once the user/patient operates a key pad provided on the case body 100 to set the device in the inhale mode for forcedly supplying the air to the patient and then operates the device, the air pressure generating unit 200 is driven at a rotational speed corresponding to a preset pressure to suction the air through the air inlet 210 and simultaneously discharge the air through the air outlet 220.

Here, the air inlet 210 communicates through the second vertical passage 313 of the housing 310 and the second vertical passage 313 communicates with the receiving space 311. In the inhale mode, at this time, the rotating body 340 is placed such that the first partition 343 can communicate the first vertical passage 312 with the second vertical passage 313 and the second partition 344 can communicate the first horizontal passage 314 connected to the relaying hose 400 with the second horizontal passage 315 connected to the air outlet 220.

Through the above structure, the fresh air outside of the case body 100 flows by air pressure generated in the air pressure generating unit 200 and opens the one-way valve part 130 of the case body provided on the closing plate 120 of the case body 100. This fresh air flows and then enters the air inlet 210 via the first vertical passage 312, the first direct passage 345 of the rotating body 340 and the second vertical passage 313.

Subsequently, the fresh air having entered the air inlet 210 enters the relaying hose 400 via the air outlet 220, the second horizontal passage 315, the third direct passage 347 of the rotating body 340 and the first horizontal passage 314.

Then, the fresh air having entered the relaying hose 400 flows the mask hose 150 and is forcedly inhaled into the respiratory organ of the patient.

By means of the sensing means, at this time, the user/patient can recognize that the current mode of the device is the inhale mode.

Referring to FIG. 15, if the patient performing the cough inducing process determines that the air pressure in the inhale mode is excessive, by rotating and placing the rotating body 340 between the inhale mode and the pause mode at a desired angle (that is, the half-inhale mode), half of the first partition 343 of the rotating body 340 is overlapped by the second vertical passage 313 of the housing 310 and a half of the second partition 344 of the rotating body 340 is overlapped by the second horizontal passage 315 of the housing 310 so that some of air flowing and being suctioned through the second horizontal passage 315 flows toward the second direct passage 346 of the rotating body 340. Thus, a pressure of the air inhaled forcedly into a patient's respiratory organ can be adjusted.

Referring to FIGS. 16A and 16B, in the exhale mode after the inhale mode, the rotating body 340 is rotated and placed such that the second partition 344 of the rotating body 340 can communicate the first horizontal passage 314 connected to the relaying hose 400 with the second vertical passage 313 connected to the air inlet 210 and the first partition 343 of the rotating body 340 can communicate the second horizontal passage 315 connected to the air inlet 210 with the third horizontal passage 316 connected to the one-way valve part 320 for the housing.

Through the above structure, if a command for operating the inhale assisting device of the present invention is input, the air pressure generating unit 200 is driven at a rotational speed corresponding to a preset pressure to suction the air through the air inlet 210 and simultaneously discharge the air through the air outlet 220.

Due to the above, the air is forcedly discharged through the mask hose 150 communicating with the respiratory organ of a patient and the air which is forcedly discharged enters the first horizontal passage 314 of the housing 310 via the relaying hose 400.

Then, the discharged air entering the first horizontal passage 314 enters the air inlet 210 via the third direct passage 347 of the rotating body 340 and the second vertical passage 313.

Subsequently, the fresh air entering the air inlet 210 passes through the air outlet 220, the second horizontal passage 315, the first direct passage 345 of the rotating body 340 and the third horizontal passage 316 to open the one-way valve part 320 for the housing and then flows in the case body 100.

At this time, since the air which is forcedly discharged contains a cough noise generated by inducing the patient's cough, when the cough noise penetrates the case body 100, some of the cough noise contained in air which is forcedly discharged is damped and then penetrates the case body. The remainder of the cough noise of the patient, which does not penetrate the case body, is reflected and dispersed in the case body 100 or damped and penetrates the case body 100 again to minimize the cough noise of the patient.

Simultaneously, since carbon dioxide and an odor causing substance contained in a cough of the patient remains in the case body 100 and gradually spreads to an outside, when the device is subsequently utilized for inducing a patient's cough, an absorption of carbon dioxide and an odor causing substance contained in a cough of the patient into the air supplied from an outside is minimized.

At this time, the user/patient can also recognize whether the current mode is the exhale mode through the sensing means.

Referring to FIGS. 17A and 17B, in the pause mode after the exhale mode, once the rotating body 340 is rotated such that the second direct passage 346 of the rotating body 340 can communicate the second horizontal passage 315 connected to the air outlet 220 with the second vertical passage 313 connected to the air inlet 210, the first partition 343 of the rotating body 340 blocks the first vertical passage 312, the second partition 344 of the rotating body 340 blocks the first horizontal passage 314, and the upper hole 348 for normal respiration of the rotating body 340, the relaying hole 332 for normal respiration of the receiving body 330 and the lower hole 318 for normal respiration of the housing 310 overlap to allow the first horizontal passage 314 to communicate with the first vertical passage 312.

Due to the above, the air flowing due to air pressure of the air pressure generating unit 200, that is, air flowing into the air inlet 210 and simultaneously discharged to the air outlet 220 repeatedly and endlessly flows due to the second horizontal passage 315, the second direct passage 346 and the second vertical passage 313 communicating with other.

Because of this, in the pause mode, although air pressure is generated through the air pressure generating unit 200, the air is not supplied to the patient's respiratory organ or an outside, and the above structure guides to allow the patient to breathe naturally.

In other words, if the air is inhaled through the mask hose 150 communicating with the patient's respiratory organ, the one-way valve part 130 for the case body provided on the closing plate 120 of the case body 100 is opened by an inhaling force of the patient so that the fresh air in an outside enters the relaying hose 400 via the first vertical passage 312, the upper hole 348 for normal respiration, the relaying hole 332 for normal respiration, the lower hole 318 for normal respiration and the first horizontal passage 314.

Subsequently, the fresh air entering the relaying hose 400 flows into the mask hose 150 and then is naturally inhaled into the patient's respiratory organ.

Then, if the patient exhales air, the air which is naturally discharged is enters the first vertical passage 312 via the mask hose 150, the relaying hose 400, the first horizontal passage 314, the upper hole 348 for normal respiration, the relaying hole 332 for normal respiration and the lower hole 318 for normal respiration.

At this time, since the air entering the first vertical passage 312 and naturally discharged presses the one-way valve part 130 of the case body, this air closes the one-way valve part 130 of the case body and flows into the third horizontal passage 316. Then, the air flows in the case body 100 in a state in which the one-way valve part 130 for the housing is opened by this air so that the patient can breathe naturally in the pause mode.

Through a repetition of the processes in the inhale mode, the exhale mode and the pause mode as illustrated above, the cough of the patient is induced.

By means of the sensing means, at this time, the user/patient can recognize that the current mode of the device is the pause mode.

In addition, in a case of a routine patient who is subject to a cough inducing function and has healthy lungs or is not sensitive, although the time required for forcedly inhaling the air is the same as that required for forcedly exhaling the air under the preset air pressure, it is possible to induce a patient's cough, while in a case of a specific patient who has weak lungs or is sensitive, a relatively great amount of time is consumed for forcedly inhaling the air. Thus, there is a need to provide a function by which a small quantity of air per unit time is inhaled without damaging a lung and the air flow is adjusted so as to allow the air to be rapidly and forcedly exhaled under the preset air pressure to induce a cough.

To this end, an air-inflow rate adjusting means 500 is mounted to the cough assisting device of the present invention, the air-inflow rate adjusting means divides the relaying hose 400 into a front relaying hose 410 and a rear relaying hose 420, both sides of which are connected to one side of the front relaying hose 410 and one side of the rear relaying hose 420, respectively. According to a selection, the air-inflow rate adjusting means 500 adjusts only a flow rate of the air flowing through the front relaying hose 410 communicating with a relaying entrance of the direction switching valve unit 300 under a certain air pressure.

The air-inflow rate adjusting means 500 performing the above function mainly consists of a body for air flow, a shut-off valve part 540, a one-way valve part 550 and a direction switching valve part 560.

First, the body for air flow is divided into an upper body 510 for air flow and a lower body 520 for air flow, and a partition 530 is provided between the upper body 510 for air flow and the lower body 520 for air flow to form a space divided into a first chamber 511 and a second chamber 521 acting as air-flow paths.

At this time, a first air-flow port 512 communicating with the front relaying hose 410 is provided on one side of an outer surface of the upper body 510 for air flow of the first chamber 511, and an upper tube-connecting port 513 is provided on the other side of the outer surface the upper body 510 having a space formed therein.

In addition, the partition 530 disposed between the upper body 510 for air flow and the lower body 520 for air flow has a large-sized inlet hole 531, a small-sized inlet hole 532 and an outlet hole 533 formed thereon and sequentially arranged.

At this time, two (2) large-sized inlet holes 531 may be formed as shown in the drawings or various numbers of the large-sized inlet holes such as one or three (3) large-sized inlet holes may be formed according to an air flow.

Furthermore, at this time, a second air-flow port 522 communicating with the rear relaying hose 420 is provided on one side of an outer surface of the lower body 520 for air flow of the second chamber 521, and a lower tube-connecting port 523 is provided on the other side of the outer surface the lower body 520 having a space formed therein.

In addition, a lower connecting part 524 protrudes from an inner surface of the lower body 520 for air flow and corresponds to the large-sized inlet hole 531 of the partition 530. At this time, the lower body 520 for air flow is disposed such that the lower connecting part 524 and the lower tube-connecting port 523 communicate with each other.

The shut-off valve part 540 is provided for opening or closing the large-sized inlet hole 531 according to a pressure difference between the first chamber 511 and the second chamber 521 and coupled to the lower connecting part 524 of the lower body 520 for air flow.

The shut-off valve part 540 consists of a contact region 541 to be in contact with the large-sized inlet hole 561 by an elastic force and an elastic-pressurized corrugation region 542 having a sectional area larger than that of the contact region 541 and being elastically pressurized by a pressure difference. At this time, the elastic-pressurized corrugation region 542 of the shut-off valve part 540 communicates with the direction switching valve part 560.

As one example, a diaphragm formed of an elastic material may be employed as the shut-off valve part 540.

The one-way valve part 550 is a member for opening/closing the outlet hole 533. In particular, the one-way valve part 550 is a one-way valve which is opened when the air in the second chamber 521 flows into the first chamber 511 and is closed when the air in the first chamber 511 flows into the second chamber 521.

The one-way valve part 550 performing the above function is formed of an elastic material and may consist of a rubber plate 552, and one side of the rubber plate is fixedly installed on one side surface of the partition 530 placed in the first chamber 511 through a fixing protrusion 551 to allow the rubber plate to open the outlet hole 533 by means of air pressure.

At this time, the rubber plate 552 has an area larger than that of the outlet hole 533.

Due to the above, if air flowing from the second chamber 521 collides with the rubber plate 552 formed of a highly elastic material and having a thin membrane-shape, the rubber plate 552 is lifted up in the counterclockwise direction with respect to the fixing protrusion 551 fixed to the partition 530 to enable the air to flow toward the first chamber 511.

The direction switching valve part 560 is connected to the first and second chambers 511 and 521 formed on the upper body 510 for air flow and the lower body 520 for air flow, and this direction switching valve part communicates the first and second chambers 511 and 521 with each other or blocks the first chamber and discharges the air in the second chamber in response to an operating signal. If the first and second chambers 511 and 521 communicate with each other through the direction switching valve part 560, since a pressure in the second chamber 521 is larger than that in the first chamber 511, the shut-off valve part 540 closes the large-sized inlet hole 531 so that the air in the first chamber 511 flows toward the second chamber 521 via the small-sized inlet hole 532.

As one embodiment, a solenoid valve which is 3-port 2-position type valve consisting of a pressure-input port P, a pressure-output port A and an exhausting port R may be employed as of the direction switching valve part performing the above function.

The direction switching valve part 560 is connected to the body for air flow by means of an upper tube 570 communicating with an upper tube-connecting port 513 and the pressure inlet port P through both ends thereof and a lower tube 580 communicating with an lower tube-connecting port 523 and the pressure outlet port A through both ends thereof.

For a routine patient who has healthy lungs or is not sensitive, by using the air-inflow rate adjusting means 500 having the above structure, the time required for forcedly suctioning air in the preset air pressure becomes the same as that required for forcedly discharging air. Also, for a specific patient who has weak lungs or is sensitive, compared to the time required for forcedly discharging air, much more time is consumed for forcedly suctioning air in the preset air pressure (that is, an amount of air which is forcedly suctioned per unit time becomes less than an amount of air which is forcedly discharged per unit time) so that when the patient forcedly inhales the air, it is possible to induce to cough without serious damage to the patient's lung.

The above processes for inducing a patient to cough are illustrated with reference to the drawings as below.

Referring to FIG. 20, in the inhale mode in which air is forcedly suctioned for inducing a cough for a routine patient who has healthy lungs or is not sensitive, the direction switching valve part 560 is switch-operated, for example, off-operated (corresponding to a cough inducing function for a routine patient).

By the off operation, the direction switching valve part 560 is controlled such that the pressure-output port A and the exhausting port R communicate with each other in a state in which the pressure-input port P is closed.

Through the above operation, the air which is forcedly caused to enter through the first air-flow port 512 of the upper body 510 for air flow flows to the first chamber 511 and pressurizes the large-sized inlet hole 531 and the outlet hole 533 of the partition 530.

At this time, a pressure is also applied to the shut-off valve part 540 which is in contact with the large-sized inlet hole 531 of the partition 530 by an elastic force. Here, since the pressure-output port A and the exhausting port R communicate with each other, the elastic-pressurized corrugation region 542 constituting the shut-off valve part 540 elastically pressurizes the lower tube 580 communicating with the lower tube-connecting port 523 and the large-sized inlet hole 531 is opened to allow the air in the first chamber 511 to be guided and flow toward the second chamber 521. As a result, the air flows toward the patient's respiratory organ according to the preset air pressure.

Then, referring to FIG. 21, in the exhale mode in which air is forcedly discharged for inducing a cough for a routine patient who has healthy lungs or is not sensitive, the air forcedly caused to enter through the second air-flow port 522 of the lower body 520 for air flow flows to the second chamber 521.

At this time, since a pressure transmitted from first chamber 511 is not applied to the shut-off valve part 540, the elastic-pressurized corrugation region 542 constituting the shut-off valve part 540 is elastically restored to close the large-sized inlet hole 531 of the partition 530.

Due to the above, the air flowing to the second chamber 521 and forcedly discharged flows toward the outlet hole 533 of the partition 530, pushes the shut-off valve part 540 and flows to the first chamber through the opened outlet hole 533. Then, the air is discharged to an outside through the front relaying hose 410.

Likewise, the flow time of the air which is forcedly suctioned is substantially the same as that of the air which is forcedly discharged.

In addition, referring to FIG. 22, in the inhale mode in which air is forcedly suctioned for inducing a cough for a specific patient who has weak lungs or is sensitive, the direction switching valve part 560 is on-operated (corresponding to a cough inducing function for a specific patient).

By the on operation, the direction switching valve part 560 is controlled such that the pressure-input port P and the pressure-output port A communicate with each other.

Through the above operation, the air which is forcedly caused to enter through the first air-flow port 512 of the upper body 510 for air flow flows to the first chamber 511 as well as the second chamber 521 through the large-sized inlet hole 531 and the outlet hole 533 of the partition 530 and the upper tube 570 and the lower tube 580 communicating with each other to transmit the pressure.

At this time, since the transmitted pressure is applied to the elastic-pressurized corrugation region 542 constituting the shut-off valve part 540 through the lower tube 580, due to the contact region 541 having a sectional area smaller than that of the elastic-pressurized corrugation region 542, the pressure applied to the elastic-pressurized corrugation region 542 constituting the shut-off valve part 540 through the lower tube 580 is increased so that the contact region 541 is in contact with the large-sized inlet hole 531 of the partition 530.

Due to the above, the air which forcedly enters through the first air-flow port 512 flows only to the small-sized inlet hole 532 of the partition 530 to allow a small amount of air to flow through the small-sized inlet hole 532. Thus, much time is spent for the air, which enters under the preset air pressure, to flow to the patient's respiratory organ so that the air can be more stably supplied to a patient who has weak lungs or is sensitive.

Then, referring to FIG. 23, in the exhale mode in which air is forcedly discharged for inducing a cough for a specific patient who has weak lungs or is sensitive, the air forcedly caused to enter through the second air-flow port 522 of the lower body 520 for air flow flows to the second chamber 521.

At this time, as previously illustrated, since the first chamber 511 and the second chamber 521 communicate with each other, the state in which the contact region 541 constituting the shut-off valve part 540 is in contact with the large-sized inlet hole of the partition 530 is maintained.

In the above state, the air flowing to the second chamber 521 flows toward the outlet hole 533 of the partition 530, pushes the shut-off valve part 540 and then flows to the first chamber through the opened outlet hole 533. Then, the air is rapidly discharged to an outside through the front relaying hose 410.

In the cough assisting device of the present invention, an amount of air which is forcedly suctioned is less than that in the conventional device, but an amount of air which is forcedly discharged is the same as that in the conventional device and the air is rapidly and forcedly discharged so that when a function of cough induction is performed for a patient who has weak lungs or is sensitive, the same cough induction function can be performed without damage to a lung.

The cough assisting device of the present invention is advantageous in that the passage formed in the rotating body constituting the device for controlling an inflow and discharge of the air is subdivided into three (3) sub-passages to allow the air to enter and be discharged along the shortest paths so that the rotating body is miniaturized to reduce a driving electric power to be consumed for rotating/driving the miniaturized rotating body as compared with a conventional device.

In addition, the cough assisting device of the present invention guides the air forcedly discharged from a patient's respiratory organ to allow the air to flow into the case body so that when a cough noise contained in the air forcedly discharged from a patient's respiratory organ collides with the case body, some of the cough noise is damped and then penetrates the case body and the remainder of the cough noise of the patient, which does not penetrate the case body, is reflected and dispersed in the case body or damped and penetrates the case body again to minimize the cough noise and to minimize reabsorption of carbon dioxide and an odor causing substance contained in a cough of the patient into air supplied from an outside when the device is repeatedly utilized for inducing the patient to cough.

Also, the cough assisting device of the present invention can adjust an amount of air that is forcedly suctioned in the preset air pressure so that, even though the time required for forcedly suctioning air in the preset air pressure is the same as that required for forcedly discharging air, it is possible to induce a routine patient, who has healthy lungs or is not sensitive, to cough. Furthermore, for a specific patient who has weak lungs or is sensitive, compared to the time required for forcedly discharging air, much more time is consumed for forcedly suctioning air in the preset air pressure (that is, an amount of air which is forcedly suctioned per unit time is less than an amount of air which is forcedly discharged per unit time) so that when the patient forcedly inhales the air, it is possible to induce coughing without serious damage to the patient's lung.

While the direction switching valve unit and the cough assisting device using the same of the invention, which are not limited to the above-mentioned embodiment, have been shown and described with reference to certain example embodiments thereof, it will be understood by those skilled in the art that various changes in form and details may be made therein without departing from the spirit and scope of the invention as defined by the appended claims.

What is claimed is:

1. A direction switching valve unit, comprising:
 a housing (310) having a receiving space (311) formed near a central part of an upper surface of the housing (310), a first vertical passage (312) formed for communicating an outside of a lower surface with the receiving space (311), a second vertical passage (313) formed for communicating the receiving space (311) with an outside of a first side surface, a first horizontal passage (314) formed for communicating the receiving space (311) with one side part of the upper surface, a second horizontal passage (315) formed for communicating the receiving space (311) with an outside of a second side surface opposite to the first side surface, and a third horizontal passage (316) formed for communicating the first vertical passage (312) with an opened portion of the upper surface;

a receiving body (330) fixed in the receiving space (311) of the housing (310) and having communication ports (331) formed at and penetrating locations corresponding to four (4) opened portions of the receiving space (311);

a rotating body (340) placed on the receiving body (330), the rotating body having an upper plate (341), a lower plate (342) and first and second partitions (343) and (344) connecting the upper plate (341) and the lower plate (342) to form a first direct passage (345), a second direct passage (346) and a third direct passage (347), both sides of each of the direct passages being opened; and a two-directional motor (350) provided at an upper side of the housing (310) and connected to a shaft of the rotating body (340).

2. The direction switching valve unit of claim 1, further comprising a one-way valve part (320) for the housing for opening/closing the opened portion of the third horizontal passage (316) to allow air in the third horizontal passage (316) to flow only to an outside.

3. The direction switching valve unit of claim 1, wherein:
the housing (310) has a horizontal partition (317) provided therein to enable the receiving body (330) to be secured to the horizontal partition (317) in a state in which the receiving body (330) lies on the horizontal partition (317),
the lower plate (342) on which the third direct passage (347) is formed has an upper hole (348) for normal respiration,
the receiving body (330) has a relaying hole (332) for normal respiration corresponding to the upper hole (348) for normal respiration of the rotating body (340), the relaying hole (332) being formed on a bottom surface of the receiving body (330), and
the horizontal partition (317) has a lower hole (318) for normal respiration corresponding to the relaying hole (332) for normal respiration of the receiving body (330).

4. A cough assisting device, comprising
a case body (100) having an inhaling space (110) formed on and passing through a lower surface of the case body (100);
an air pressure generating unit (200) provided in the case body (100), the air pressure generating unit generating an air pressure through a rotation force for suctioning air into an air inlet (210) and discharging suctioned air via an air outlet (220);
a direction switching valve unit (300) provided in the inhaling space (110) formed in the case body (100), the direction switching valve unit converting a flow direction of the air so that air is forcedly suctioned toward a patient's respiratory organ or forcedly discharged from a patient's respiratory organ by the air pressure generated in the air pressure generating unit (200);

a connecting port (140) secured to and passing through the case body (100), the connecting port communicating with a mask hose (150) through a first side of the connecting port; and a relaying hose (400) provided in the case body (100), the relaying hose communicating with a second side of the connecting port (140) through a first end of the relaying hose, the second side being opposite to the first side, the relaying hose communicating with the direction switching valve unit (300) through a second end of the relaying hose;

wherein the direction switching valve unit (300) comprises
a housing (310) provided in the inhaling space (110) formed in the case body (100) and having a receiving space (311) formed on an upper surface of the housing, a first vertical passage (312) formed for communicating the inhaling space (110) with the receiving space (311), a second vertical passage (313) formed for communicating the receiving space (311) with an air inlet (210) of the air pressure generating unit (200), a first horizontal passage (314) formed for communicating the receiving space (311) with the relaying hose (400), a second horizontal passage (315) formed for communicating the receiving space (311) with an air outlet (220) of the air pressure generating unit (200), and a third horizontal passage (316) formed for communicating the first vertical passage (312) with an opened portion of the upper surface;

a receiving body (330) fixed in the receiving space (311) of the housing (310) and having communication ports (331) formed at and penetrating locations corresponding to four (4) opened portions of the receiving space (311);

a rotating body (340) placed on the receiving body (330), the rotating body having an upper plate (341), a lower plate (342) and first and second partitions (343) and (344) connecting the upper plate (341) and the lower plate (342) to form a first direct passage (345), a second direct passage (346) and a third direct passage (347), both sides of each of the direct passages being opened; and a two-directional motor (350) provided at an upper side of the housing (310) and connected to a shaft of the rotating body (340).

5. The cough assisting device of claim 4, further comprising a one-way valve part (320) for the housing for opening/closing the opened portion of the third horizontal passage (316) to allow air in the third horizontal passage (316) to flow only to an outside of the third horizontal passage.

6. The cough assisting device of claim 4, wherein:
the housing (310) has a horizontal partition (317) provided therein to enable the receiving body (330) to be secured to the horizontal partition (317) in a state in which the receiving body (330) lies on the horizontal partition (317),
the lower plate (342) on which the third direct passage (347) is formed has an upper hole (348) for normal respiration formed thereon,
the receiving body (330) has a relaying hole (332) for normal respiration corresponding to the upper hole (348) for normal respiration of the rotating body (340), the relaying hole (332) being formed on a bottom surface of the receiving body (330), and
the horizontal partition (317) has a lower hole (318) for normal respiration, corresponding to the relaying hole (332) for normal respiration of the receiving body (330).

7. The cough assisting device of claim 4, further comprising a closing plate (120) for closing the inhaling space (110) of the case body (100), the closing plate having an opening (121) formed thereon.

8. The cough assisting device of claim 7, further comprising a one-way valve part (130) for the case body for opening/closing the opening (121) of the closing plate (120) to allow air to enter the first vertical passage (312).

9. The cough assisting device of claim 4, further comprising an air-inflow rate adjusting means (500) dividing the relaying hose (400) into a front relaying hose (410) and a rear relaying hose (420), the air-inflow rate adjusting means being connected to one side of the front relaying hose (410) and one side of the rear relaying hose (420), the air-inflow rate adjusting means adjusting only a flow rate of the air flowing through the front relaying hose (410) communicating with a first horizontal passage (314) of the direction switching valve unit (300) under a certain air pressure according to a selection.

10. The cough assisting device of claim 9, wherein the air-inflow rate adjusting means (500) comprises
 a body for air flow divided into first and second chambers (511 and 521) by a partition (530) on which a large-sized inlet hole (531), a small-sized inlet hole (532) and an outlet hole (533) are formed, the body for air flow having first and second air-flow ports (512 and 522) communicating therewith for allowing the air to enter and be discharged;
 a shut-off valve part (540) provided for opening or closing the large-sized inlet hole (531) according to a pressure difference between the first chamber (511) and the second chamber (521);
 a one-way valve part (550) provided for opening/closing the outlet hole (553) and for allowing the air in the second chamber (521) to flow only to the first chamber (511); and
 a direction switching valve part (560) connected to the first and second chambers (511) and (521) for communicating the first and second chambers (511) and (521) with each other or blocking the first chamber and discharging air in the second chamber to an outside of the second chamber in response to an operation signal,
 wherein, if the first and second chambers (511 and 521) are communicated with each other by the direction switching valve part (560), a pressure in the second chamber (521) is larger than that in the first chamber (511) so that the shut-off valve part (540) closes the large-sized inlet hole (531) to allow the air in the first chamber (511) to flow toward the second chamber (521) via the small-sized inlet hole (532).

11. The cough assisting device of claim 10, wherein the shut-off valve part (540) comprises a contact region (541) provided at a location toward the second chamber (521) and being in contact with the large-sized inlet hole (531) by an elastic force; and an elastic-pressurized corrugation region (542) having a sectional area larger than that of the contact region (541) and being elastically pressurized by a pressure difference.

12. The cough assisting device of claim 11, wherein the elastic-pressurized corrugation region (542) of the shut-off valve part (540) communicates with the direction switching valve part (560).

13. The cough assisting device of claim 10, wherein the direction switching valve part is a solenoid valve which is a 3-port 2-position valve.

14. The cough assisting device of claim 10, wherein the first air-flow port (512) is connected to one side of the front relaying hose (410) and the second air-flow port (522) is connected to one side of the rear relaying hose (420).

* * * * *